United States Patent
Ma et al.

(10) Patent No.: US 10,995,377 B2
(45) Date of Patent: May 4, 2021

(54) GENETIC LOCUS ASSOCIATED WITH PHYTOPHTHORA ROOT AND STEM ROT IN SOYBEAN

(71) Applicants: CORTEVA AGRISCIENCE LLC, Indianapolis, IN (US); Purdue Research Foundation, West Lafayette, IN (US)

(72) Inventors: Jianxin Ma, West Lafayette, IN (US); Jieqing Ping, Apex, IN (US); Joshua C. Fitzgerald, Lafayette, IN (US); Chunbao Zhang, Changchun (CN); Feng Lin, Changchun (CN); Yonghe Bai, Westfield, IN (US); Maqsood Rehman, Indianapolis, IN (US); Oswald Crasta, Carmel, IN (US); Rajat Aggarwal, Zionsville, IN (US); Ananta Acharya, Carmel, IN (US)

(73) Assignees: CORTEVA AGRISCIENCE LLC, Indianapolis, IN (US); PURDUE RESEARCH FOUNDATION

(*) Notice: Subject to any disclaimer, the term of this patent is extended or adjusted under 35 U.S.C. 154(b) by 0 days.

(21) Appl. No.: 15/171,709

(22) Filed: Jun. 2, 2016

(65) Prior Publication Data
US 2018/0030550 A1   Feb. 1, 2018

Related U.S. Application Data

(60) Provisional application No. 62/170,441, filed on Jun. 3, 2015.

(51) Int. Cl.
| | | |
|---|---|---|
| C12Q 1/68 | (2018.01) | |
| A01H 1/04 | (2006.01) | |
| A01H 1/00 | (2006.01) | |
| C12N 15/29 | (2006.01) | |
| A01H 6/54 | (2018.01) | |
| A01H 5/10 | (2018.01) | |
| C12Q 1/6895 | (2018.01) | |
| C12Q 1/6827 | (2018.01) | |
| C07K 14/415 | (2006.01) | |

(52) U.S. Cl.
CPC ............ *C12Q 1/6895* (2013.01); *A01H 1/04* (2013.01); *A01H 6/542* (2018.05); *C12Q 1/6827* (2013.01); *A01H 1/00* (2013.01); *A01H 5/10* (2013.01); *C07K 14/415* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 7,507,874 B2 * | 3/2009 | Han | A01H 1/04 800/260 |
| 2004/0034888 A1 | 2/2004 | Liu et al. | |
| 2004/0261144 A1 | 12/2004 | Martin et al. | |
| 2007/0283459 A1 | 12/2007 | Byrum et al. | |
| 2008/0127361 A1 | 5/2008 | St. Martin et al. | |
| 2012/0174246 A1 | 7/2012 | Chaky et al. | |
| 2013/0198912 A1 * | 8/2013 | Hudson | C07K 14/415 800/302 |
| 2014/0178867 A1 | 6/2014 | Chaky et al. | |
| 2014/0206032 A1 | 7/2014 | Baley et al. | |

FOREIGN PATENT DOCUMENTS

WO    2011097492    8/2011

OTHER PUBLICATIONS

Song et al. Crop Science 50: 1950-1960 (Oct. 2010).*
Song et al. Theoretical and Applied Genetics 109: 122-128 (2004).*
Zhang et al. Theoretical and Applied Genetics 126: 1555-1561 (2013).*
Gordon et al. Crop Science 46: 168-173 (2006).*
Lin et al. Theoretical and Applied Genetics 126: 2177-2185 (2013).*
Ping et al. Theoretical and Applied Genetics 129: 445-451 (published online Dec. 10, 2015).*
Lin et al. BMC Genomics, vol. 15, Article No. 18, pp. 1-13 (Jan. 2014).*
Cregan et al. Crop Science 39: 1464-1490 (1999).*
Glyma_07g07270 (from SoyBase, Glyma 1.0 soybean genetic map, available Dec. 2010).*
Glyma_07g062900 (from SoyBase, Glyma 2.0 soybean genetic map, available Feb. 2013).*
Satt463 (from SoyBase, Glyma 1.0 and 2.0 soybean genetic maps, available Dec. 2010 and Feb. 2013).*
Satt540 (from SoyBase, Glyma 1.0 and 2.0 soybean genetic maps, available Dec. 2010 and Feb. 2013).*
PI 594527 (downloaded from GRIN database, available 1996).*
BARCSOYSSR_07_0300 (from SoyBase Glyma 1.0 and 2.0 soybean genetic maps, available Dec. 2010 and Feb. 2013).*
BARCSOYSSR_07_0320 (from SoyBase Glyma 1.0 and 2.0 soybean genetic maps, available Dec. 2010 and Feb. 2013).*
Michelmore et al. PNAS USA 88: 9828-9832 (1991).*
Song et al. PLOS One, vol. 8, No. 1, article No. e54985, pp. 1-12 (2013).*
Dorrance et al. (2008) "Isolation, storage, palhotype characterization, and evaluation of resistance for Phytophthora sojae" in Soybean Plant Health Progress, 10:1094.
Allen et al. (2006) "A modified protocol for rapid DNA isolation from plant tissues using cetyltrimethylammonium bromide" Nature Protocols, 1:2320-2325.

(Continued)

*Primary Examiner* — David T Fox

(57) ABSTRACT

The present subject matter relates to methods and compositions for identifying soybean plants that having increased *Phytophthora* root and stem rot resistance. The methods use molecular markers to identify and to select plants with increased *Phytophthora* root and stem rot resistance or to identify and deselect plants with decreased *Phytophthora* root and stem rot resistance. Soybean plants generated by the methods disclosed are also a feature of the present subject matter.

13 Claims, 3 Drawing Sheets

Figure 1:
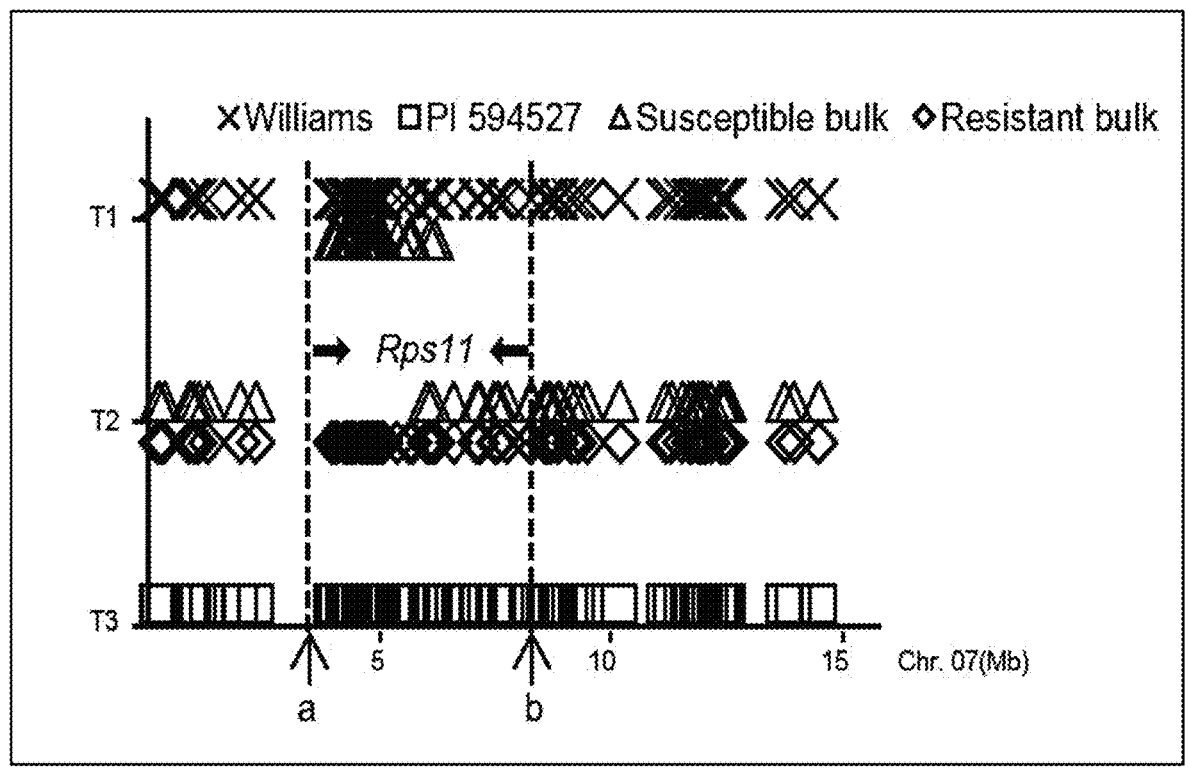

Specification includes a Sequence Listing.

(56) References Cited

OTHER PUBLICATIONS

International Search Report and Written Opinion for PCT/US2016/035507, dated Sep. 8, 2016.
Demirbas et al. "Simple Sequence Repeat Markers Linked to the Soybean Rps Genes for Phytophthora Resistance", Crop Science, (2001), vol. 41, pp. 1220-1227.
Hegstad et al. "Identifying Resistance to Phytophthora sojae in Selected Soybean Accessions Using RFLP Techniques", Crop Science, (1998), vol. 38, pp. 50-55.
Kim et al. "Fine Mapping the Soybean Aphid Resistance Gene Rag1 in Soybean", Theor Appl Genet., (2009), vol. 120, No. 5, pp. 1063-1071.

* cited by examiner

SEQUENCE LISTING

```
<160> NUMBER OF SEQ ID NOS: 60

<210> SEQ ID NO 1
<211> LENGTH: 121
<212> TYPE: DNA
<213> ORGANISM: Glycine max

<400> SEQUENCE: 1
aatgggcgtg cacagttatc agttatcagt tatcattccc tattttgtag tcttaattgt      60
rgggtcagtt tcgtacctct ctagttacat gttaaaatca atcctctcta ctgtgttaca     120
c                                                                      121

<210> SEQ ID NO 2
<211> LENGTH: 121
<212> TYPE: DNA
<213> ORGANISM: Glycine max

<400> SEQUENCE: 2
atatgtgaag gtgaatggaa tggtattggt tgttgtactt atgaggcacc agcagccaac      60
rtattcataa taacgtggag gatcagtgat aatatgaaac tcgagcctaa ggtgaatggt     120
t                                                                      121

<210> SEQ ID NO 3
<211> LENGTH: 121
<212> TYPE: DNA
<213> ORGANISM: Glycine max

<400> SEQUENCE: 3
tggatgaacc aaacccattg aagcttctat catgcagtaa tatttccact aatcatcagt      60
rgaaggacaa gttttctcac tacaggcaca aactatgatt tttttccttc tgatttgatt     120
``` a                                                                      121

<210> SEQ ID NO 4
<211> LENGTH: 121
<212> TYPE: DNA
<213> ORGANISM: Glycine max

<400> SEQUENCE: 4
attctcgaat ctttcctggg ccagcccatt gaggtttttc tttttggacc ggcccatatc      60
ycactatcac tccactcttc ctttctcttg ccctacctca gaaacccaca ctccaaaacc     120
a                                                                     121

<210> SEQ ID NO 5
<211> LENGTH: 121
<212> TYPE: DNA
<213> ORGANISM: Glycine max

<400> SEQUENCE: 5
tagatttgaa ttgatataga tatatgggtg attattaatt aatatgccag ctcttaccca      60
yaaatagtct taattaaact aaaagaaaag gaaattaaga tctcattgta aaataaaag      120 g                                                                     121

<210> SEQ ID NO 6
<211> LENGTH: 121
<212> TYPE: DNA
<213> ORGANISM: Glycine max

<400> SEQUENCE: 6 tgggggtgg gaggttcttg gaaagataag tggttgctta ttcattatgc catctcgcat       60
ycctttttgg aggttttgat tggttgttgt acagacagga ctgacagccg aagaggttta    120
t                                                                     121

<210> SEQ ID NO 7
<211> LENGTH: 121
<212> TYPE: DNA
<213> ORGANISM: Glycine max

<400> SEQUENCE: 7
tttatcattt gttttatatt tacatacttc gcctaactaa acgtatttaa aagaaatatg      60
ytaataattt aaaattataa tttgtaaatt aaaatctatt aattatttaa aagtgtgatt    120
a                                                                     121

<210> SEQ ID NO 8
<211> LENGTH: 121
<212> TYPE: DNA
<213> ORGANISM: Glycine max

<400> SEQUENCE: 8
caagtggtgg caaagagtgg agatggggca acctgatgat tcttttaggg acgtacgttt      60
ycccactcta gagtgtgtat gtgtttgctc gtgttgggag ttcaatagct gcaatcacta    120
c                                                                     121

<210> SEQ ID NO 9
<211> LENGTH: 121
<212> TYPE: DNA
<213> ORGANISM: Glycine max

```
<400> SEQUENCE: 9
tgtcaccatc taccggcatg ggaggcaaag aatccgcatc acctttttacc ccatacattc    60 ycctcatggc ttctgagaaa gcaaaccttc actcaaacac aaatgaagag aaaatcaagc   120
t                                                                   121

<210> SEQ ID NO 10
<211> LENGTH: 121
<212> TYPE: DNA
<213> ORGANISM: Glycine max

<400> SEQUENCE: 10
gtagttttga acttttgata actacaattt cgctatcaat aaaagtgtat gcccttttaat   60 yatagagcag tacttcccctt tcttggttat caaaatggat ggtgataaat tgtcttattt  120
t                                                                   121

<210> SEQ ID NO 11
<211> LENGTH: 121
<212> TYPE: DNA
<213> ORGANISM: Glycine max

<400> SEQUENCE: 11
gcggcggcgg caaccctaaa attcgataca agcaagtaca cagtcgcagc tccttttata    60
rtgagcgttt tggttcaaat gctagtgcag aaacccaaaa cattcccaaa tttatttaat  120
t                                                                   121

<210> SEQ ID NO 12
<211> LENGTH: 121
<212> TYPE: DNA
<213> ORGANISM: Glycine max

<400> SEQUENCE: 12
catgccatgt tttttaaaaa catttaaaga aaaaataaat attaagcaga tggtatacga    60
kaaattattg tataatccca gatcaccatg gtattggtca atctaacaaa tgccaagttt  120
a                                                                   121

<210> SEQ ID NO 13
<211> LENGTH: 121
<212> TYPE: DNA
<213> ORGANISM: Glycine max

<400> SEQUENCE: 13
aatcttacca tttttgcaatg tcataggctg ggatatatag ttttttggtta tctaactaat  60 rcatatatta tgttattgct ttgaaggcat caaaggagat gaacaaaata catactgaat  120
t                                                                   121

<210> SEQ ID NO 14
<211> LENGTH: 121
<212> TYPE: DNA
<213> ORGANISM: Glycine max

<400> SEQUENCE: 14
gatcggaggt gctcaacaag gttcgggtaa aggtgttgtt cgtggagttc ttgggctgcc    60
kggccgcctg gttggaggca tcttgggagg aagttcgact gatgctgctg caaatgcggg  120
a                                                                   121
```

```
<210> SEQ ID NO 15
<211> LENGTH: 121
<212> TYPE: DNA
<213> ORGANISM: Glycine max

<400> SEQUENCE: 15
acatttgttt cttatgtaca acagtgttac agtggcaaca agtatagaat ttaagatatt      60
ktgtaaaata cttaaacttt acttctctag gcctgtccgt agtgattttg cttaaaactt     120
t                                                                    121

<210> SEQ ID NO 16
<211> LENGTH: 121
<212> TYPE: DNA
<213> ORGANISM: Glycine max

<400> SEQUENCE: 16
aattctagat ttggaatgaa aggggcttg gaattttggt tgggcgtgtg gcacagatga      60
raaggatgtg tgcgacaaat catatagaac tgtgggacct aactggagtt gtacatgtgc    120
a                                                                    121

<210> SEQ ID NO 17
<211> LENGTH: 121
<212> TYPE: DNA
<213> ORGANISM: Glycine max

<400> SEQUENCE: 17
cttctaacag cttgtctgtt ttgactgtac ctgcacacaa actttccatc ctctcgcaaa     60
rgaatactgt gaattcctcc aaggacggga aacttaaact cccttttgtag aaccttctca   120 g                                                                    121

<210> SEQ ID NO 18
<211> LENGTH: 121
<212> TYPE: DNA
<213> ORGANISM: Glycine max

<400> SEQUENCE: 18
tctcaaataa ccttatgcta aggaatccaa ccaccactaa ccgctaaata taattagaat     60
kattattcaa atagataata tttcttacat atatatcatt gctttagtga aatagtaagt    120
g                                                                    121

<210> SEQ ID NO 19
<211> LENGTH: 121
<212> TYPE: DNA
<213> ORGANISM: Glycine max

<400> SEQUENCE: 19
ctgttccagt atttcttgct gatatctgtg gatggggttg gatggttata taggtttccg     60
yggcgacaac aatatcatcg cagatatccc gaattttctt gacaaatctg atgcaaggt    120 a                                                                    121

<210> SEQ ID NO 20
<211> LENGTH: 121
<212> TYPE: DNA
<213> ORGANISM: Glycine max

<400> SEQUENCE: 20
cagaatttat tttagagact agctatagca aggcttgtgg ctaagccagt taccttcctg     60
```

```
mgagtgaact tgagaaagta cagaggctag ctaaggtagg tattagtcta cctaaacctg    120
a                                                                    121

<210> SEQ ID NO 21
<211> LENGTH: 121
<212> TYPE: DNA
<213> ORGANISM: Glycine max

<400> SEQUENCE: 21
gaagacatta tcgggtccac tgtaaaatta attgtttgtt ctactattgt ggacaacaca    60
ractccattc tttcagcttg attttcttgt acagtgacta catctcttct cgaaataaaa    120
a                                                                    121

<210> SEQ ID NO 22
<211> LENGTH: 121
<212> TYPE: DNA
<213> ORGANISM: Glycine max

<400> SEQUENCE: 22
gcggtttgaa ggtggcggtg gtgaggtcct gtcttggtgt tctaggtatt ttgaaggaga    60
rgagaatggg gatggtgtag ctcttgccat gtggttgggg tttggcacga ggtcatgatg    120
g                                                                    121

<210> SEQ ID NO 23
<211> LENGTH: 121
<212> TYPE: DNA
<213> ORGANISM: Glycine max

<400> SEQUENCE: 23
caaaaaaact tcatctggac tagtggctcc atatcttatg caagttaatt ggagataaat    60
ycacgctctc taaaatttcg catttttaac ttacaagcac gtgcacattt gaattactct    120
g                                                                    121

<210> SEQ ID NO 24
<211> LENGTH: 121
<212> TYPE: DNA
<213> ORGANISM: Glycine max

<400> SEQUENCE: 24
gttttgaagc ttgccgcttt gggtaagggg ccaacagtaa agacacagta gatatattga    60
maagatctct ggtggtcatg cggaacaggt ttatccacca aatctttttt tttttttttt    120
t                                                                    121

<210> SEQ ID NO 25
<211> LENGTH: 121
<212> TYPE: DNA
<213> ORGANISM: Glycine max

<400> SEQUENCE: 25
tccttaacac ccttaccgca gttacttgcc gcctcaatcc attgctgaaa tgaatgctca    60
yaaataaata tatttgcagg ctacgaatct ctgctcctag attttgtttt cttaattatt    120
t                                                                    121

<210> SEQ ID NO 26
<211> LENGTH: 121
<212> TYPE: DNA
<213> ORGANISM: Glycine max
```

<400> SEQUENCE: 26

```
aacaaacgaa ttcttggact tgttgctatg tacagtctag caactttaag aaacacgggt      60
ygtagtaagc atgacactat tacaaaagtc cttttaaaga tacttttcac aatagttcgc     120
c                                                                    121
```

<210> SEQ ID NO 27
<211> LENGTH: 121
<212> TYPE: DNA
<213> ORGANISM: Glycine max

<400> SEQUENCE: 27

```
taaaatattt aaaagaaaaa gaaaagaaa tgagggttta aaatagaagt acaaattaaa      60
mattatcgaa aaatgaaatt agtatgcaat ataataaatg gaaccatttt cactttcacc    120
a                                                                    121
```

<210> SEQ ID NO 28
<211> LENGTH: 121
<212> TYPE: DNA
<213> ORGANISM: Glycine max

<400> SEQUENCE: 28

```
acaacttgaa gagtttattt aatcaatgtc aatcatggca aagggtgagg aatggcttgg      60
rttaaatggg atttggttgc ttcacccatt gacatggggg gttggggatt aaaaatttag    120
a                                                                    121
```

<210> SEQ ID NO 29
<211> LENGTH: 121
<212> TYPE: DNA
<213> ORGANISM: Glycine max

<400> SEQUENCE: 29

```
ttgccgtgag attcactgga aatggtttac attagtatgt gtcgagaaac aattagttcc      60
rattatcctt gcttttttaa actgttgtcc atgctatcat cttctttgaa ccatattgta    120
a                                                                    121
```

<210> SEQ ID NO 30
<211> LENGTH: 121
<212> TYPE: DNA
<213> ORGANISM: Glycine max

<400> SEQUENCE: 30

```
gcatgcatac actggtatac atgtcaatgc ttgaattgtt ttgatcacag tggttttgt      60
rtatctttc agattggctt atcttcatga aggtcttgaa ccaaaagttg tccaccgaga    120
t                                                                    121
```

<210> SEQ ID NO 31
<211> LENGTH: 121
<212> TYPE: DNA
<213> ORGANISM: Glycine max

<400> SEQUENCE: 31

```
atagaaggtg gtagaatctg gctgaaggca tggcagcagg cagctgtggc agtgggttcc      60
rcggtggggg cgttgttgga ccctcgaaga gcagatttga tagcagctct tggtgagacc    120
a                                                                    121
```

<210> SEQ ID NO 32
<211> LENGTH: 121
<212> TYPE: DNA
<213> ORGANISM: Glycine max

<400> SEQUENCE: 32
aatcagttaa gatttctgga cacgtacaaa gaaggttaca agaaatgctt atgaggaatg    60
yagattagaa gatttctagt catataaaag gatagaagga ggagaccaag aagaatgtta   120
a                                                                  121

<210> SEQ ID NO 33
<211> LENGTH: 121
<212> TYPE: DNA
<213> ORGANISM: Glycine max

<400> SEQUENCE: 33
cttgcctatc ggcagtccat catagttctc gcctatattg gcacctcgcc tatatcagcg    60
rcatctatga aggggaatgt tagaaagtct cacacgcctg attcgttctt tggatgcaac   120
t                                                                  121

<210> SEQ ID NO 34
<211> LENGTH: 20
<212> TYPE: DNA
<213> ORGANISM: Artificial Sequence
<220> FEATURE:
<223> OTHER INFORMATION: 'BARCSOYSSR_07_0241 forward primer

<400> SEQUENCE: 34
caaacaaggc cgcttaaatc                                               20

<210> SEQ ID NO 35
<211> LENGTH: 22
<212> TYPE: DNA
<213> ORGANISM: Artificial Sequence
<220> FEATURE:
<223> OTHER INFORMATION: BARCSOYSSR_07_0241 reverse primer

<400> SEQUENCE: 35
tccttaaaac atgctcatgg aa                                            22

<210> SEQ ID NO 36
<211> LENGTH: 20
<212> TYPE: DNA
<213> ORGANISM: Artificial Sequence
<220> FEATURE:
<223> OTHER INFORMATION: BARCSOYSSR_07_0266 forward primer

<400> SEQUENCE: 36
ctgtcaagtg aggcaccaaa                                               20

<210> SEQ ID NO 37
<211> LENGTH: 20
<212> TYPE: DNA
<213> ORGANISM: Artificial Sequence
<220> FEATURE:
<223> OTHER INFORMATION: BARCSOYSSR_07_0266 reverse primer

<400> SEQUENCE: 37
cccccatgct tgttctctta                                               20

<210> SEQ ID NO 38
<211> LENGTH: 20

```
<212> TYPE: DNA
<213> ORGANISM: Artificial Sequence
<220> FEATURE:
<223> OTHER INFORMATION: BARCSOYSSR_07_0275 forward primer

<400> SEQUENCE: 38
actactcacc ggccaaaatg                                               20

<210> SEQ ID NO 39
<211> LENGTH: 20
<212> TYPE: DNA
<213> ORGANISM: Artificial Sequence
<220> FEATURE:
<223> OTHER INFORMATION: BARCSOYSSR_07_0275 reverse primer

<400> SEQUENCE: 39
cacactcgat cgatatccca                                               20

<210> SEQ ID NO 40
<211> LENGTH: 20
<212> TYPE: DNA
<213> ORGANISM: Artificial Sequence
<220> FEATURE:
<223> OTHER INFORMATION: BARCSOYSSR_07_0278 forward primer

<400> SEQUENCE: 40
ggggatcgaa aatgtcttcc                                               20

<210> SEQ ID NO 41
<211> LENGTH: 20
<212> TYPE: DNA
<213> ORGANISM: Artificial Sequence
<220> FEATURE:
<223> OTHER INFORMATION: BARCSOYSSR_07_0278 reverse primer

<400> SEQUENCE: 41
gacaaccgtc catcatgaca                                               20

<210> SEQ ID NO 42
<211> LENGTH: 20
<212> TYPE: DNA
<213> ORGANISM: Artificial Sequence
<220> FEATURE:
<223> OTHER INFORMATION: BARCSOYSSR_07_0286 forward primer

<400> SEQUENCE: 42
aaaaatcagc acccatcgac                                               20

<210> SEQ ID NO 43
<211> LENGTH: 20
<212> TYPE: DNA
<213> ORGANISM: Artificial Sequence
<220> FEATURE:
<223> OTHER INFORMATION: BARCSOYSSR_07_0286 reverse primer

<400> SEQUENCE: 43
agccctggcc ttattttgtt                                               20

<210> SEQ ID NO 44
<211> LENGTH: 20
<212> TYPE: DNA
<213> ORGANISM: Artificial Sequence
<220> FEATURE:
<223> OTHER INFORMATION: BARCSOYSSR_07_0295 forward primer

<400> SEQUENCE: 44
```
ctctcctttc attccccaca    20

<210> SEQ ID NO 45
<211> LENGTH: 20
<212> TYPE: DNA
<213> ORGANISM: Artificial Sequence
<220> FEATURE:
<223> OTHER INFORMATION: BARCSOYSSR_07_0295 reverse primer

<400> SEQUENCE: 45
ttcttggagc ttcggaggta    20

<210> SEQ ID NO 46
<211> LENGTH: 20
<212> TYPE: DNA
<213> ORGANISM: Artificial Sequence
<220> FEATURE:
<223> OTHER INFORMATION: BARCSOYSSR_07_0300 forward primer

<400> SEQUENCE: 46
tcgcaatatt ggctacgatg    20

<210> SEQ ID NO 47
<211> LENGTH: 26
<212> TYPE: DNA
<213> ORGANISM: Artificial Sequence
<220> FEATURE:
<223> OTHER INFORMATION: BARCSOYSSR_07_0300 reverse primer

<400> SEQUENCE: 47
ctgaaaacaa aataaaagag aacaaa    26

<210> SEQ ID NO 48
<211> LENGTH: 22
<212> TYPE: DNA
<213> ORGANISM: Artificial Sequence
<220> FEATURE:
<223> OTHER INFORMATION: BARCSOYSSR_07_0320 forward primer

<400> SEQUENCE: 48
tttaactgaa aatactccgg ca    22

<210> SEQ ID NO 49
<211> LENGTH: 24
<212> TYPE: DNA
<213> ORGANISM: Artificial Sequence
<220> FEATURE:
<223> OTHER INFORMATION: BARCSOYSSR_07_0320 reverse primer

<400> SEQUENCE: 49
tcataattta agagaccaaa ccga    24

<210> SEQ ID NO 50
<211> LENGTH: 22
<212> TYPE: DNA
<213> ORGANISM: Artificial Sequence
<220> FEATURE:
<223> OTHER INFORMATION: BARCSOYSSR_07_0339 forward primer

<400> SEQUENCE: 50
cgcaaggtct aatattcact cg    22

<210> SEQ ID NO 51
<211> LENGTH: 23
<212> TYPE: DNA
<213> ORGANISM: Artificial Sequence
<220> FEATURE:
<223> OTHER INFORMATION: BARCSOYSSR_07_0339 reverse primer

<400> SEQUENCE: 51
aaaactgatt gcaggagatt agc                                    23

<210> SEQ ID NO 52
<211> LENGTH: 21
<212> TYPE: DNA
<213> ORGANISM: Artificial Sequence
<220> FEATURE:
<223> OTHER INFORMATION: BARCSOYSSR_07_0289 forward primer

<400> SEQUENCE: 52
ggcaaaaggt aaaaagggtt t                                      21

<210> SEQ ID NO 53
<211> LENGTH: 20
<212> TYPE: DNA
<213> ORGANISM: Artificial Sequence
<220> FEATURE:
<223> OTHER INFORMATION: BARCSOYSSR_07_0289 reverse primer

<400> SEQUENCE: 53
tccccaaact ttcatcatgt                                        20

<210> SEQ ID NO 54
<211> LENGTH: 121
<212> TYPE: DNA
<213> ORGANISM: Glycine max

<400> SEQUENCE: 54
gtagttttga actttgata actacaattt cgctatcaat aaaagtgtat gcccttta at        60 yatagagcag tacttccctt tcttggttat caaaatggat ggtgataaat tgtcttattt       120
t                                                                      121

<210> SEQ ID NO 55
<211> LENGTH: 21
<212> TYPE: DNA
<213> ORGANISM: Artificial Sequence
<220> FEATURE:
<223> OTHER INFORMATION: InDel_2 forward primer

<400> SEQUENCE: 55
ctccattctt ttgagtcgag t                                      21

<210> SEQ ID NO 56
<211> LENGTH: 22
<212> TYPE: DNA
<213> ORGANISM: Artificial Sequence
<220> FEATURE:
<223> OTHER INFORMATION: InDel_2 reverse primer

<400> SEQUENCE: 56
actcagggcg gatcccaaag tg                                     22

<210> SEQ ID NO 57
<211> LENGTH: 24
<212> TYPE: DNA
<213> ORGANISM: Artificial Sequence
<220> FEATURE:
<223> OTHER INFORMATION: InDel_1 forward primer

<400> SEQUENCE: 57

```
aataaattta ttttggaatg tatc                                           24

<210> SEQ ID NO 58
<211> LENGTH: 22
<212> TYPE: DNA
<213> ORGANISM: Artificial Sequence
<220> FEATURE:
<223> OTHER INFORMATION: InDel_1 reverse primer

<400> SEQUENCE: 58
tttatgttga tcccaacatg ta                                             22

<210> SEQ ID NO 59
<211> LENGTH: 25
<212> TYPE: DNA
<213> ORGANISM: Artificial Sequence
<220> FEATURE:
<223> OTHER INFORMATION: BARCSOYSSR_07_0297 forward primer

<400> SEQUENCE: 59
ttgtctatca aaatttaacc acgaa                                          25

<210> SEQ ID NO 60
<211> LENGTH: 22
<212> TYPE: DNA
<213> ORGANISM: Artificial Sequence
<220> FEATURE:
<223> OTHER INFORMATION: BARCSOYSSR_07_0297 reverse primer

<400> SEQUENCE: 60
tccacatgtg cactgttagt gt                                             22
```

GENETIC LOCUS ASSOCIATED WITH PHYTOPHTHORA ROOT AND STEM ROT IN SOYBEAN

CROSS REFERENCE TO RELATED APPLICATIONS

The present application claims priority to U.S. Provisional Application No. 62/170,441, filed Jun. 3, 2015, which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "77970-US-NP_20160601_Seq_Listing.txt", created on Jun. 1, 2016, and having the size of 15.7 kilobytes, and is filed concurrently with the specification. The sequence listing contained in this ASCII formatted document is part of the specification, and is incorporated herein by reference in its entirety.

FIELD OF THE DISCLOSURE

The presently-disclosed subject matter relates to methods useful in increasing resistance to *Phytophthora* root and stem rot in soybean plants.

BACKGROUND

*Phytophthora* root and stem rot (PRSR), caused by the soil borne pathogen *Phytophthora sojae*, has been reported in most soybean growing areas throughout the world, since it was first noted in Indiana in 1948 and again in Ohio in 1951 (Dorrance et al. 2007; Erwin and Ribeiro 1996; Kaufmann and Gerdemann 1958; Schmitthenner 1985). PRSR was ranked as the second most destructive soybean disease after soybean cyst nematode (SCN) that suppressed soybean yield in the United States from 1996 to 2009, which caused the annual yield losses of 44.7 million bu (Koenning and Wrather 2010; Wrather and Koenning 2009).

Deployment of race-specific resistant soybean cultivars has been the primary strategy for the management of PRSR as it is highly effective and economically and environmentally safe in reducing soybean yield losses from *Phytophthora* disease (Dorrance et al. 2007; Dorrance and Schmitthenner 2000; Schmitthenner 1999). To date, approximately 25 Rps genes/alleles have been identified, distributing at 19 loci across eight different chromosomes. Chromosome 3 (Chr. 3) (MLG N) has the most Rps genes/alleles mapped, including Rps1a, Rps1b, Rps1c, Rps1d, Rps1k, Rps7, Rps9, RpsUN1, RpsYu25, RpsYD29, and an unnamed Rps gene reported in a Japanese cultivar 'Waseshiroge' (Demirbas et al. 2001; Fan et al. 2009; Gao et al. 2005; Lin et al. 2013; Sugimoto et al. 2011; Sun et al. 2011; Weng et al. 2001; Wu et al. 2011a; Yao et al. 2010; Zhang et al. 2013). Two Rps genes, Rps2 and RpsUN2, have been mapped at the end of Chr. 16 (MLG J), which is a well-known resistance gene cluster region (Kanazin et al. 1996; Lin et al. 2013; Polzin et al. 1994). Interestingly, Rps3 (containing three alleles 3-a, 3-b, 3-c) and Rps 8 have been mapped to another resistance gene rich region on Chr. 13 (MLG F) (Demirbas et al. 2001; Gordon et al. 2006). RpsJS, a recently identified Rps gene, is linked with Rps4, Rps5, and Rps6 and all of which are located on the short arm of Chr. 18 (MLG G) (Demirbas et al. 2001; Sandhu et al. 2004; Sun et al. 2014). In addition, RpsYB30, Rps ZS18, RpsSu and Rps10 have been mapped to Chr. 19 (MLG L), Chr. 2 (MLG D1b), Chr. 10 (MLG O) and Chr. 17 (MLG D2), respectively (Wu et al. 2011b; Yao et al. 2010; Zhang et al. 2013; Zhu et al. 2007).

Many of these Rps genes have already been successfully deployed in soybean breeding programs to control PRSR. Nevertheless, these genes may only be effective for 8 to 15 years due to the rapid and continuous evolving of the pathogen under selection pressures (Schmitthenner 1985). In addition, pyramiding known Rps genes into a single cultivar may not be an effective long-term breeding strategy because a recombining pathogen population could create new combinations of virulence alleles as rapidly as breeders can stack resistance genes (McDonald and Linde 2002). Therefore, identifying novel Rps genes is still needed to effectively manage *Phytophthora* disease.

A novel *Phytophthora* resistance locus is identified in this disclosure. In addition, markers linked to the disclosed novel *Phytophthora* resistance locus are also identified. Markers that are linked to the novel *Phytophthora* resistance locus include SSR, InDel and SNP markers. The markers identified in this disclosure can be used for *Phytophthora* resistance genotyping to support a breeding program. Using the presently disclosed markers to perform *Phytophthora* resistance genotyping in support of a breeding program provides, among other benefits: cost and time savings; early selection of desired progeny; and more accurate and rapid commercialization of *Phytophthora* resistant soybean varieties. Candidate genes underlying the phenotype for the novel *Phytophthora* resistance locus disclosed herein are also described.

SUMMARY

In one embodiment, methods of identifying a soybean plant that displays increased resistance to PRSR, comprising detecting in germplasm of the soybean plant at least one allele of a marker locus are provided. The marker locus is on chromosome 7, and is located within a chromosomal interval comprising and flanked by BARC_1_01_Gm07_5383355_C_T and BARC_1_01_Gm07_5629128_A_C, and the at least one allele is associated with increased resistance to PRSR. In some specific embodiments, the marker locus can be selected from any of the following marker loci: BARC_1_01_Gm07_5383355_C_T, BARCSOYSSR_07_0286, BARCSOYSSR_07_0289, BARC_1_01_Gm07_5442375_T_C, BARC_1_01_Gm07_5457696_C_T, Gm07_5480878_G_A, BARC_1_01_Gm07_5481829_T_C, BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel_2, InDel_1, BARCSOYSSR_07_0297, BARC_1_01_Gm07_5555040_T_G, BARC_1_01_Gm07_5580414_T_C, BARC_1_01_Gm07_5762798_C_T, BARC_1_01_Gm07_5599140_A_C, BARC_1_01_Gm07_5601844_G_A, BARC_1_01_Gm07_5610838_T_C, BARCSOYSSR_07_0300, and BARC_1_01_Gm07_5629128_A_C, as well as any other marker that is linked to these markers. In some embodiments, the marker locus is on chromosome 7, and is located within the interval comprising and flanked by BARCSOYSSR_07_0295 and InDel_1, and comprises at least one allele that is associated with increased resistance to PRSR. In some specific embodiments, the marker locus can be selected from any of the following marker loci: BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel2 and InDel_1, as well as any other marker that is linked to these markers. In some embodiments, the marker locus comprises a gene selected from the group consisting of Glyma.07G62500, Glyma.07G62600, Glyma.07G62700, Glyma.07G62800, and Glyma.07G62900. Soybean plants identified by this method are also of interest.

In another embodiment, methods for identifying soybean plants with increased resistance to PRSR by detecting a haplotype in the germplasm of the soybean plant are provided. The haplotype comprises alleles at one or more marker loci, wherein the one or more marker loci are found on chromosome 7 within the interval comprising and, flanked by, BARC_1_01_Gm07_5383355_C_T and BARC_1_01_Gm07_5629128_A_C. In some specific embodiments, the marker locus can be selected from any of the following marker loci: BARC_1_01_Gm07_5383355_C_T, BARCSOYSSR_07_0286, BARCSOYSSR_07_0289, BARC_1_01_Gm07_5442375_T_C, BARC_1_01_Gm07_5457696_C_T, Gm07_5480878_G_A, BARC_1_01_Gm07_5481829_T_C, BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel_2, InDel_1, BARCSOYSSR_07_0297, BARC_1_01_Gm07_5555040_T_G, BARC_1_01_Gm07_5580414_T_C, BARC_1_01_Gm07_5762798_C_T, BARC_1_01_Gm07_5599140_A_C, BARC_1_01_Gm07_5601844_G_A, BARC_1_01_Gm07_5610838_T_C, BARCSOYSSR_07_0300, and BARC_1_01_Gm07_5629128_A_C, as well as any other marker that is linked to these markers. In some embodiments, the haplotype comprises alleles at one or more marker loci, wherein the one or more marker loci are found on chromosome 7 within the interval comprising and, flanked by BARCSOYSSR_07_0295 and InDel_1. In some specific embodiments, the marker locus can be selected from any of the following marker loci: BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel_1 and InDel_1, as well as any other marker that is linked to these markers. The haplotype is associated with increased resistance to PRSR. In some embodiments, the marker locus comprises a gene selected from the group consisting of Glyma.07G62500, Glyma.07G62600, Glyma.07G62700, Glyma.07G62800, and Glyma.07G62900. Soybean plants identified by this method are also of interest.

In a further embodiment, methods of selecting plants with increased resistance to PRSR are provided. In one aspect, a first soybean plant is obtained that has at least one allele of a marker locus wherein the allele is associated with increased resistance to PRSR. The marker locus can be found on chromosome 7, within the interval comprising and flanked by BARC_1_01 Gm07_5383355 C_T and BARC_1_01_Gm07_5629128_A_C, and in some specific embodiments the marker locus can be found within the interval comprising and flanked by BARCSOYSSR_07_0295 and InDel_1. The first soybean plant can be crossed to a second soybean plant, and the progeny resulting from the cross can be evaluated for the allele of the first soybean plant. Progeny plants that possess the allele from the first soybean plant can be selected as having increased resistance to PRSR. In some embodiments, the marker locus comprises a gene selected from the group consisting of Glyma.07G62500, Glyma.07G62600, Glyma.07G62700, Glyma.07G62800, and Glyma.07G62900. Soybean plants selected by this method are also of interest.

BRIEF DESCRIPTION OF FIGURES AND SEQUENCE LISTING

The present subject matter can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984) which are herein incorporated by reference in their entirety. The symbols and format used for nucleotide and amino acid sequence data comply with the rules set forth in 37 C.F.R. § 1.822.

FIG. 1 illustrates the location for Rps11 based on the dissimilar SNP distribution between the resistant and susceptible bulks. The y-axis indicates three different types of SNPs on Chr. 07. T1 represents SNPs are homozygous as the susceptible alleles in Williams. T3 represents SNPs are homozygous as the resistant alleles in PI 594527. T2 represents SNPs are heterozygous with alleles from both parents. The x-axis shows the physical position of the SNPs. The interval between a and b indicates the potential region for Rps11.

Figure 2:
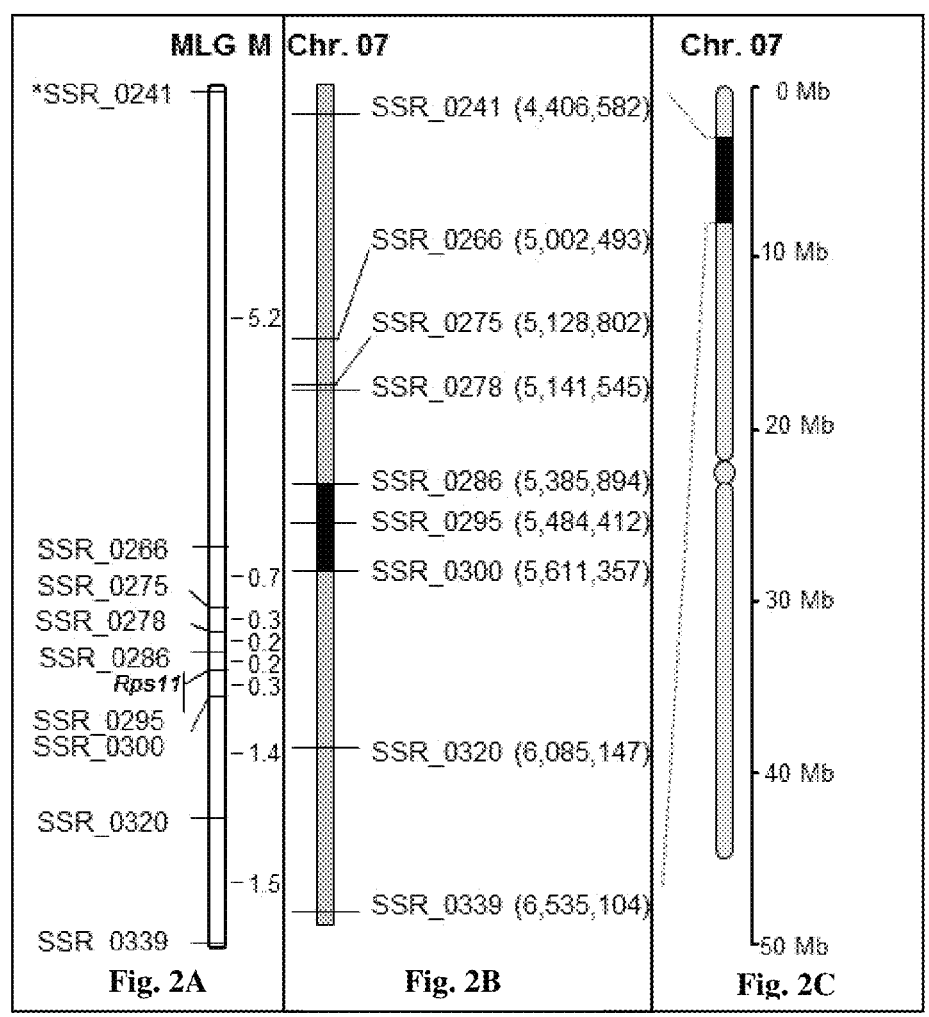

FIG. 2 illustrates the genetic and physical maps of Rps11 on Chr. 7. FIG. 2(a) is a genetic linkage map of Rps11. Marker names are listed on the left and genetic distances (cM) are on the right. *abbreviation for 'BARCSOYSSR_07_0241'. FIG. 2(b) shows physical positions of SSR markers determined by BLAST searching their primer sequences against soybean reference genome (Glyma1.1) on the SoyBase website. Numbers in brackets represent start position of the markers in base pairs (bp). The interval of Rps11 is highlighted with black color. FIG. 2(c) shows physical location of the Rps11 interval in the Williams 82 reference genome. The bars indicate two arms of Chr. 07, and the circle indicates approximate position of the centromeric region.

Figure 3:
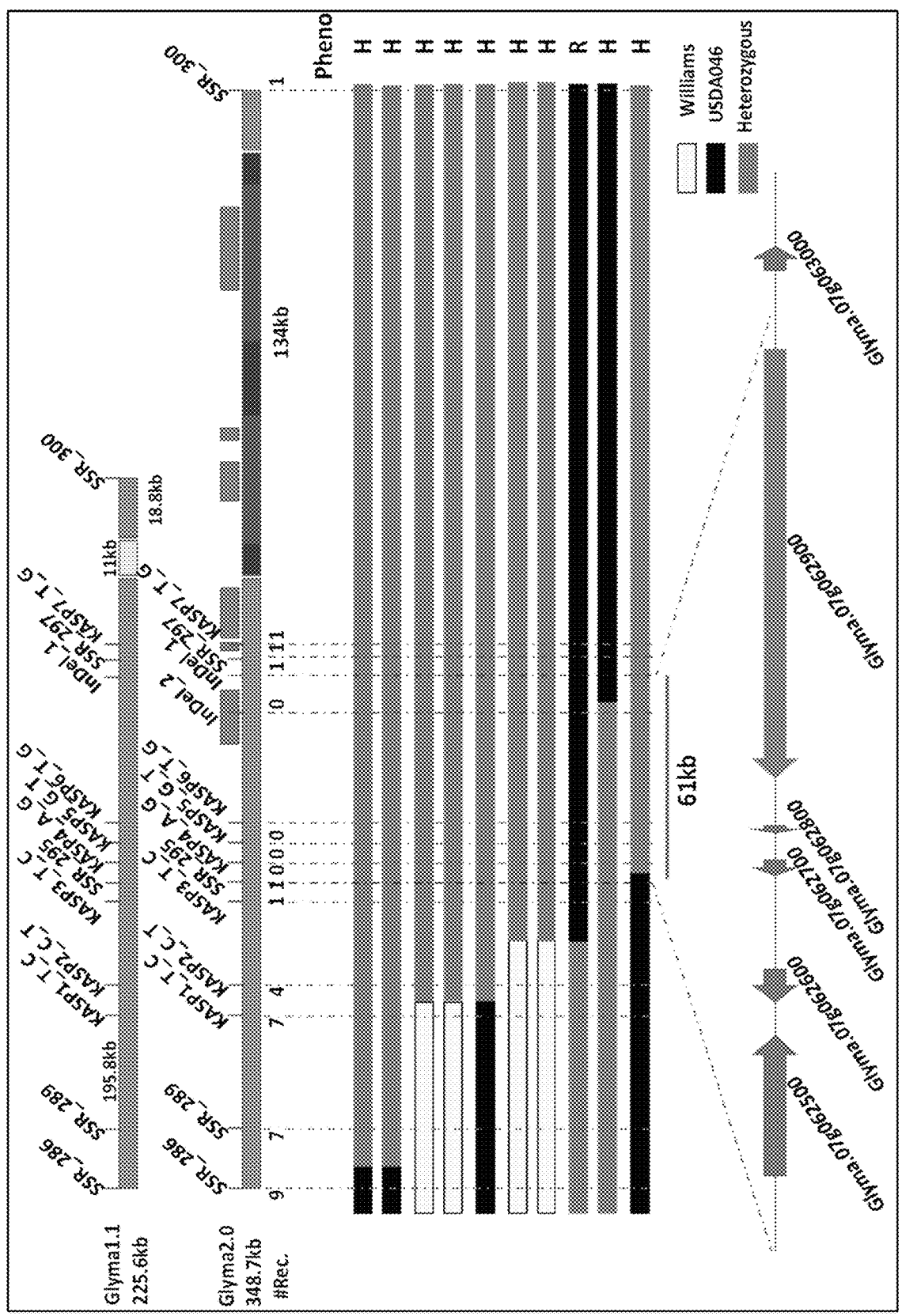

FIG. 3 illustrates the 61 kb region on chromosome 7 containing the Rps11 locus, associated markers, and five gene models predicted in the region. The maps of 10 F3 recombinants are shown.

SEQ ID NOs: 1-33, and 54 are the sequences flanking and including the SNPs used to design assays on the SoySNP8K BeadChip and/or for KASP™ genotyping.

SEQ ID NOs: 34-53 and 55-60 are the forward and reverse primers for the SSR markers mapped on chromosome 7.

DETAILED DESCRIPTION

The present subject matter provides methods for identifying and selecting soybean plants with increased resistance to PRSR. The following definitions are provided as an aid to understand the subject matter disclosed herein.

Definitions

The term "allele" refers to one of two or more different nucleotide sequences that occur at a specific locus. An allele is "associated with" a trait when it is linked to it and when the presence of the allele is an indicator that the desired trait or trait form will occur in a plant comprising the allele.

"Backcrossing" refers to the process used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

A centimorgan ("cM") is a unit of measure of recombination frequency. One cM is equal to a 1% chance that a marker at one genetic locus will be separated from a marker at a second locus due to crossing over in a single generation.

"Chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The term "chromosomal interval" designates any and all intervals defined by any of the markers set forth in the presently disclosed subject matter. A chromosomal interval that correlates with increased resistance to PRSR is provided. This interval, located on chromosome 7, comprises and is flanked by BARC_1_01_Gm07_5383355_C_T and BARC_1_01_Gm07_5629128_A_C. A subinterval of chromosomal interval BARC_1_01_Gm07_5383355_C_T and BARC_1_01_Gm07_5629128_A_C is BARCSOYSSR_07_0295 and InDel_1.

The term "complement" refers to a nucleotide sequence that is complementary to a given nucleotide sequence, i.e., the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased resistance to PRSR, or alternatively, is an allele that allows the identification of plants with decreased resistance to PRSR that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of molecular genetic markers (also called "molecular markers," "genetic markers" or simply "markers"). A genetic map is a product of the mapping population, types of markers used, and the polymorphic potential of each marker between different populations. The order and genetic distances between loci can differ from one genetic map to another. However, information such as marker position and order can be correlated between maps by determining the physical location of the markers on the chromosome of interest, using a soybean reference genome, such as for example, Glyma1.1, which is publicly available on the SoyBase website. One of ordinary skill in the art can use a publicly available genome browser to determine the physical location of markers on a chromosome.

The term "genetic marker" shall refer to any type of nucleic acid based marker, including but not limited to, Restriction Fragment Length Polymorphism (RFLP), Simple Sequence Repeat (SSR) Random Amplified Polymorphic DNA (RAPD), Cleaved Amplified Polymorphic Sequences (CAPS) (Rafalski and Tingey, 1993, Trends in Genetics 9:275-280), Amplified Fragment Length Polymorphism (AFLP) (Vos et al, 1995, Nucleic Acids Res. 23:4407-4414), Single Nucleotide Polymorphism (SNP) (Brookes, 1999, Gene 234:177-186), Sequence Characterized Amplified Region (SCAR) (Pecan and Michelmore, 1993, Theor. Appl. Genet, 85:985-993), Sequence Tagged Site (STS) (Onozaki et al. 2004, Euphytica 138:255-262), Single Stranded Conformation Polymorphism (SSCP) (Orita et al., 1989, Proc Natl Aced Sci USA 86:2766-2770). Inter-Simple Sequence Repeat (ISR) (Blair et al. 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple led, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

The term "heterozygous" means a genetic condition wherein different alleles reside at corresponding loci on homologous chromosomes.

The term "homozygous" means a genetic condition wherein identical alleles reside at corresponding loci on homologous chromosomes.

"Hybridization" or "nucleic acid hybridization" refers to the pairing of complementary RNA and DNA strands as well as the pairing of complementary DNA single strands.

The term "hybridize" means the formation of base pairs between complementary regions of nucleic acid strands.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a quantitative trait loci (QTL), a transgene, or the like. In any case, offspring comprising the desired allele can be repeatedly backcrossed to a line having a desired genetic background and selected for the desired allele, to result in the allele becoming fixed in a selected genetic background. For example, the chromosome 7 locus described herein may be introgressed into a recurrent parent that is susceptible to PRSR. The recurrent parent line with the introgressed gene or locus then has increased resistance to PRSR.

As used herein, the term "linkage" or "linked" is used to describe the degree with which one marker locus is associated with another marker locus or some other locus (for example, a PRSR locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units for cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits for both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., increased resistance to PRSR. The degree of linkage of a molecular marker to a phenotypic trait is measured, e.g. as a statistical probability of co-segregation of that molecular marker with the phenotype.

Linkage disequilibrium is most commonly assessed using the measure $r^2$, which is calculated using the formula described by Hill, W. G. and Robertson, A, Theor Appl. Genet 38:226-231 (1988). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie at al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Locus" and "marker locus" are used interchangeably herein and mean a position on a chromosome where a gene and/or marker is located.

As used herein, the term "mapping population" may refer to a plant population used for gene mapping. Mapping populations are typically obtained from controlled crosses of parent genotypes. Decisions on the selection of parents and mating design for the development of a mapping population, and the type of markers used, depend upon the gene to be mapped, the availability of markers, and the molecular map. The parents of plants within a mapping population must have sufficient variation for the trait(s) of interest at both the nucleic acid sequence and phenotype level. Variation of the parents' nucleic acid sequence is used to trace recombination events in the plants of the mapping population. The availability of informative polymorphic markers is dependent upon the amount of nucleic acid sequence variation.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of soybean molecular markers are known in the art, and are published or available from various sources, such as the SoyBase internet resource.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (or MAS) is a process by which phenotypes are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic add sequence or molecule that can be used to identify the presence of a marker locus, e.g., a nucleic acid probe that is complementary to a marker locus sequence, through nucleic add hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e. genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate. "G" for guanylate or deoxyguanylate. "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to a new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "non-significant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "single nucleotide polymorphism (SNP)" is a DNA sequence variation occurring when a single nucleotide—A, T, C or G—in the genome (or other shared sequence) differs between members of a biological species or paired chromosomes in an individual. For example, two sequenced DNA fragments from different individuals, AAGCCTA to AAGCTTA, contain a difference in a single nucleotide.

The term "soybean plant" includes: whole soybean (*Glycine max*) plants, soybean plant cells, soybean plant protoplast, soybean plant cell or soybean tissue cultures from which soybean plants can be regenerated, soybean plant calli, and soybean plant cells that are intact in soybean plants or parts of soybean plants, such as soybean seeds, soybean hulls, soybean flowers, soybean cotyledons, soybean leaves, soybean stems, soybean buds, soybean roots, soybean root tips, and the like.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50 of the probes are occupied at equilibrium), Stringent conditions will be those in which the salt concentration is less than about 1.0 M sodium ion, typically about 0.01 to 1.0 M sodium on concentration (or other salts) at pH 7.0 to 8.3, and the temperature is at least about 30° C. for short probes (e.g., 10 to 50 nucleotides) and at least about 60° C. for long probes (e.g. greater than 50 nucleotides). Stringent conditions may also be achieved with the addition of destabilizing agents such as form amide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SOS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151-153 (1989)) with the default parameters (GAP PENALTY=10, GAP LENGTH PENALTY=10), Default parameters for pairwise alignments and calculation of percent identity of protein sequences using the Clustal V method are KTUPLE=1, GAP PENALTY=3, WINDOW=5 and DIAGONALS SAVED=5. For nucleic adds these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Before describing the present subject matter in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Genetic Mapping

It has been recognized for quite some time that specific genetic loci correlating with particular phenotypes, such as increased resistance to PRSR, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or "MAS").

A variety of methods well known in the art are available for detecting molecular markers or clusters of molecular markers that co-segregate with a trait of interest, such as increased resistance to PRSR. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each, marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Markers Associated with PRSR Resistance

Markers associated with PRSR resistance are identified herein. The methods involve detecting the presence of at least one marker allele associated with the enhanced resistance in the germplasm of a soybean plant. The marker locus can be selected from any of the marker loci provided in Table 6, including BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, and InDel_1, and any other marker linked to these markers (linked markers can be determined from the publicly available SoyBase resource). The marker locus can be selected from any of the marker loci provided in Table 6, including BARC_1_01_Gm07_5383355_C_T, BARCSOYSSR_07_0286, BARCSOYSSR_07_0289, BARC_1_01_Gm07_5442375_T_C, BARC_1_01_Gm07_5457696_C_T, Gm07_5480878_G_A, BARC_1_01_Gm07_5481829_T_C, BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel_2, InDel_1, BARCSOYSSR_07_0297, BARC_1_01_Gm07_5555040_T_G, BARC_1_01_Gm07_5580414_T_C, BARC_1_01_Gm07_5762798_C_T, BARC_1_01_Gm07_5599140_A_C, BARC_1_01_Gm07_5601844_G_A, BARC_1_01_Gm07_5610838_T_C, BARCSOYSSR_07_0300, and BARC_1_01_Gm07_5629128_A_C and any other marker linked to this marker (linked markers can be determined from the SoyBase resource).

The genetic elements or genes located on a contiguous linear span of genomic DNA on a single chromosome are physically linked. BARC_1_01_Gm07_5383355_C_T and BARC_1_01_Gm07_5629128_A_C, both highly associated with PRSR resistance, delineate a PRSR resistance locus. Any polynucleotide that assembles to the contiguous DNA between and including SEQ ID NO:6 (the SNP source sequence for BARC_1_01_Gm07_5383355_C_T) and SEQ ID NO:24 (the SNP source sequence for BARC_1_01_Gm07_5629128_A_C) can house marker loci that are associated with PRSR resistance.

The genetic elements or genes located on a contiguous linear span of genomic DNA on a single chromosome are physically linked for the subinterval of BARCSOYSSR_07_0295 and InDel_1. BARCSOYSSR_07_0295 and InDel_1, both highly associated with PRSR resistance, delineate a PRSR resistance locus. Any polynucleotide that assembles to the contiguous DNA between and including SEQ ID NO:43 (the forward primer sequence for BARCSOYSSR_07_0295) and SEQ ID NO:58 (the reverse primer sequence for InDel_1) can house marker loci that are associated with PRSR resistance.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the markers listed in Table 4 can be used to predict PRSR resistance in a soybean plant. This includes any marker within less than 50 cM (e.g., about 10 cM, 9 cM, 8 cM, 7 cM, 6 cM, 5 cM, 4 cM, 3 cM, 2 cM, 1 cM, 0.75 cM, 0.5 cM or 0.25 cM or less) of BARC_1_01_Gm07_5383355_C_T, BARCSOYSSR_07_0286, BARCSOYSSR_07_0289, BARC_1_01_Gm07_5442375_T_C, BARC_1_01_Gm07_5457696_C_T, Gm07_5480878_G_A, BARC_1_01_Gm07_5481829_T_C, BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel_2, InDel_1, BARCSOYSSR_07_0297, BARC_1_01_Gm07_5555040_T_G, BARC_1_01_Gm07_5580414_T_C, BARC_1_01_Gm07_5762798_C_T, BARC_1_01_Gm07_5599140_A_C, BARC_1_01_Gm07_5601844_G_A, BARC_1_01_Gm07_5610838_T_C, BARCSOYSSR_07_0300, and BARC_1_01_Gm07_5629128_A_C, the markers associated with the PRSR resistance. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8% 7%, 6%, 5%, 4%, 3%, 2% 1%, 0.75%, 0.5%, 0.25%, or less) are said to be "proximal to" each other.

Although particular marker alleles can show co-segregation with increased resistance to PRSR, it is important to note that the marker locus is not necessarily responsible for the expression of the PRSR resistant phenotype. For example, it is not a requirement that the marker polynucleotide sequence be part of a gene that imparts increased resistance to PRSR (for example, be part of the gene open reading frame). The association between a specific marker allele and the increased PRSR resistance phenotype is due to the original "coupling" linkage phase between the marker allele and the allele in the ancestral soybean line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

The term "chromosomal interval" designates any and all intervals defined by any of the markers set forth in the present disclosure. A chromosomal interval that correlates with PRSR resistance is provided. This interval, located on chromosome 7, comprises and is flanked by BARC_1_01_Gm07_5383355_C_T and BARC_1_01_Gm07_5629128_A_C. A subinterval of chromosomal interval BARC_1_01_Gm07_5383355_C_T and BARC_1_01_Gm07_5629128_A_C is BARCSOYSSR_07_0295 and InDel_1.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for PRSR resistance. The interval described above encompasses a cluster of markers that co-segregate with PRSR resistance. The clustering of markers occurs in relatively small domains on the chromosomes, indicating the presence of a gene controlling the trait of interest in those chromosome regions. The interval was drawn to encompass the markers that co-segregate with PRSR resistance. The interval encompasses markers that map within the interval as well as the markers that define the termini. For example, the interval BARC_1_01_Gm07_5383355_C_T and BARC_1_01_Gm07_5629128_A_C, separated by 368,797 bp based on the Glyma2.0 reference genome, which defines a chromosomal interval encompassing a cluster of markers that co-segregate with PRSR resistance. A second example includes the subinterval, BARCSOYSSR_07_0295 and InDel_1, separated by 61,874 bp based on the Glyma2.0 reference genome, which defines a chromosomal interval encompassing a cluster of markers that co-segregate with PRSR resistance. An interval described by the terminal markers that define the endpoints of the interval will include the terminal markers and any marker localizing within that chromosomal domain, whether those markers are currently known or unknown.

Chromosomal intervals can also be defined by markers that are linked to (show linkage disequilibrium with) a marker of interest, and is a common measure of linkage disequilibrium (LD) in the context of association studies. If the $r^2$ value of LD between any chromosome 7 marker locus lying within the interval of BARC_1_01_Gm07_5383355_C_T and BARC_1_01_Gm07_5629128_A_C, the subinterval of BARCSOYSSR_07_0295 and InDel_1, or any other subinterval of BARC_1_01_Gm07_5383355_C_T and BARC_1_01_Gm07_5629128_A_C, and an identified marker within that interval that has an allele associated with increased PRSR resistance is greater than ⅓ (Ardlie et al. Nature Reviews Genetics 3:299-309 (2002)), the loci are linked.

A marker of the subject matter disclosed herein can also be a combination of alleles at marker loci, otherwise known as a haplotype. The skilled artisan would expect that there might be additional polymorphic sites at marker loci in and around the chromosome 7 markers identified herein, wherein one, or more polymorphic sites is in linkage disequilibrium (LD) with an allele associated with increased PRSR resistance. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection

Molecular markers can be used in a variety of plant breeding applications (e.g. see Staub et al. (1996) Hortscience 729-741; Tanksley (1983) Plant Molecular Biology Reporter 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. seed characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite soybean line. This is also sometimes referred to as "yield drag." The size of the flanking region can be decreased by additional backcrossing, although this is not always successful, as breeders do not have control over the size of the region or the recombination breakpoints (Young et al, (1998) Genetics 120:579-585). In classical breeding it is usually only by chance that recombinations are selected that contribute to a reduction in the size of the donor segment (Tanksley et al. (1989). Biotechnology 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will avow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with, markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of the soybean reference genome and the consensus linkage maps of the soybean genome containing increasing densities of public soybean markers have facilitated soybean genetic mapping and MAS. See, e.g. assemblies Glyma1.1 and Glyma2.0 and the Comparative *Glycine max* Consensus 4.0, which are available online on the SoyBase website.

The key components to the implementation of MAS are (i) defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as FLPs, can be used in marker assisted selection protocols.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6) Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396), SSRs are highly suited to mapping and MAS as they are multi-allelic, codominant, reproducible and amenable to high throughput automation (Rafalski et al. (1996) Generating and using DNA markers in plants. In Non-mammalian genomic analysis: a practical guide. Academic Press, pp 75-135).

Various types of SSR markers can be generated, and SSR profiles from resistant lines can be obtained by gel electrophoresis of the amplification products. Scoring of marker genotype is based on the size of the amplified fragment. An SSR service for soybean is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in soybean (Bhattramakki et al. (2002). Plant Mol Biol 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp, 475-492: Shi (2001) Clin Chem 47, pp. 164-172; Kwok (2000) Pharmacogenomics 1, pp. 95-100: Bhattramakki and Rafalski (2001) Discovery and application of single nucleotide polymorphism markers in plants. In: R, J Henry, Ed, Plant Genotyping: The DNA Fingerprinting of Plants, CABI Publishing, VVallingford. A wide range of commercially available technologies utilize these and other methods to interrogate SNPs including Masscode™. (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than, single SNPs and can be more descriptive of any particular genotype. For example, single SNP may be allele 'T' for a specific line or variety with increased PRSR resistance, but the allele 'T' might also occur in the soybean breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

The sequences for the markers listed in Table 6 can be readily used to obtain additional polymorphic SNPs (and other markers) within the chromosome interval described in this disclosure. Markers within the described map region can be hybridized to bacterial artificial chromosomes (BACs) or other genomic libraries, or electronically aligned with genome sequences, to find new sequences in the same approximate location as the described markers.

In addition to SSRs, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the soybean species, or even across other species that have been genetically or physically aligned with soybean, such as mungbean, cowpea, or common bean.

In general, MAS uses polymorphic markers that have been identified as having a significant likelihood of co-segregation with PRSR resistance. Such markers are presumed to map near a gene or genes that give the plant its PRSR resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. The means to identify soybean plants that have increased PRSR resistance by identifying plants that have a specified allele at any one of marker loci described herein, including BARC_1_01_Gm07_5383355_C_T, BARCSOYSSR_07_0286, BARCSOYSSR_07_0289, BARC_1_01_Gm07_5442375_T_C, BARC_1_01_Gm07_5457696_C_T, Gm07_5480878_G_A, BARC_1_01_Gm07_5481829_T_C, BARCSOYSSR_07_0295, BARC_1_01_Gm07_5488504_A_G, BARC_1_01_Gm07_5490895_G_T, BARC_1_01_Gm07_5495895_G_A, BARC_1_01_Gm07_5500269_T_G, BARC_1_01_Gm07_5504994_G_T, BARC_1_01_Gm07_5519521_G_A, InDel_2, InDel_1, BARCSOYSSR_07_0297, BARC_1_01_Gm07_5555040_T_G, BARC_1_01_Gm07_5580414_T_C, BARC_1_01_Gm07_5762798_C_T, BARC_1_01_Gm07_5599140_A_C, BARC_1_01_Gm07_5601844_G_A, BARC_1_01_Gm07_5610838_T_C, BARCSOYSSR_07_0300, and BARC_1_01_Gm07_5629128_A_C.

The interval presented herein finds use in MAS to select plants that demonstrate increased PRSR resistance. Any marker that maps within the chromosome 7 interval defined by and including BARC_1_01_Gm07_5383355_C_T and BARC_1_01_Gm07_5629128_A_C can be used for this purpose. In addition, haplotypes comprising alleles at one or more marker loci within the chromosome 7 interval defined by and including BARC_1_01_Gm07_5383355_C_T and BARC_1_01_Gm07_5629128_A_C can be used to introduce increased PRSR resistance into soybean lines or varieties. Any allele or haplotype that is in linkage disequilibrium with an allele associated with increased PRSR resistance can be used in MAS to select plants with increased PRSR resistance.

Candidate Genes Underlying Rps11

The development of molecular markers to perform *Phytophthora* resistance genotyping in support of a breeding program provides, among other benefits: cost and time savings; early selection of desired progeny; and more accurate and rapid commercialization of *Phytophthora* resistant soybean varieties. For commercial plant breeders the availability of high quality genetic markers that can be screened in various populations is sufficient. However, the identification of the responsible gene(s) and their allelic variation and modes of action underlying the *Phytophthora* resistance phenotypic trait provides further benefits. The identification of responsible gene(s) underlying, or associated with, phenotypic trait can overcome the limitations of marker assisted breeding using molecular markers associated with a major gene or QTL. For example, molecular markers linked to a QTL or gene of interest that are identified in one population may not be polymorphic or not as tightly linked in breeding material from a different genetic origin. Presented herein are candidate genes potentially underlying the described novel Rps11 resistance phenotype.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1: Plant Materials and Isolates of *Phytophthora sojae*

A total of 204 soybean lines allegedly conferring PRSR were selected from the USDA-ARS Soybean Collection for initial evaluation. After a first round of screening, a total of 72 lines were identified carrying resistance to both Race 17 and Race 25. Resistance to both Race 17 and Race 25 is rare among single Rps genes reported to date, and so these lines were selected as promising for multi-race resistance. The 72 lines were further narrowed to 23 lines that showed broad-spectrum PRSR after inoculation with additional *P. sojae* isolates. After further analysis, Plant Introduction (PI)

594527 was identified as a promising resistant line because of its strong and broad-spectrum resistance to P. sojae.

The mapping population consisted of 58 F2 individuals and 209 F2:3 families derived from a cross between the susceptible cultivar 'Williams' and the resistance line identified by the inventors, PI 594527. PI 594527 is a soybean line maintained by the USDA Soybean Germplasm Collection and donated from Fujian, China. PI 594527 is reported by the USDA as conferring strong resistance to a number of P. sojae isolates including race 1, race 3, race 7 and race 25, but the genetic source of that resistance was previously unknown. F1 plants were self-pollinated to generate F2 population in greenhouse. A small amount of F2 seeds were kept for initial analysis while the rest were self-pollinated in the field to develop F2:3 mapping families for both phenotype and genotype evaluations.

A set of soybean differentials were used as standard control in all inoculation experiments to ensure the isolates performed the appropriate infection (Lin et al. 2013). These differential checks were Union (Rps1-a), Harosoy 13xx (Rps1-b), Williams79 (Rps1-c), PI 103091 (Rps1-d), Williams82 (Rps1-k), L76-1988 (Rps2), L83-570 (Rps3-a), PRx146-36 (Rps3-b), PRx145-48 (Rps3-c), L85-2352 (Rps4), L85-3059 (Rps5), Harosoy 62xx (Rps6), Harosoy (Rps7), PI 399073 (Rps8) and the susceptible cultivar Williams (rps).

A total of eight P. sojae isolates with differing virulence were first used to evaluate the resistance of soybean line PI 594527. These isolates were ISA19A-1, ISA71D-1, ISA330-8, 124C-1 (race 1), pmg (10)-1 (race 10), pmg (13)-1 (race 13), pmg (17)-1 (race 17), pmg (25)-1 (race 25) and 96-13S-106A (race 28). For bulk segregation analysis and genetic mapping, the isolate 124C-1 (race 1) of P. sojae was used to obtain phenotypic data of F2 individuals and F2:3 families. Isolates were maintained on lima bean agar (LBA) medium (150 g/L Lima Beans, 2% agar).

PI 594527 was identified as a promising resistant line since it had a strong and broad-spectrum resistance to P. sojae, including race 1, race 10, race 13, race 17, race 25, race 28 and three other isolates whose pathotypes do not match any known race designation (Table 1).

the greenhouse with an average temperature of 25° C. On the 7th day of seed planting, the mycelial slurry from 14-day-old cultures grown on ½ LBA was injected into the hypocotyl of the seedling (~1 cm below cotyledons). After inoculation, seedlings were covered with plastic lid for more than 12 hours to ensure a high relative humidity during infection (out of direct sunlight). The lid was removed and the disease was allowed to develop 5-7 days (10 days maximum) before evaluation.

Reactions were recorded as resistant if the seedling was alive without expanding lesion, or susceptible if the seedling was dead with brown hypocotyl. For each F2:3 families, 12-36 progenies were scored. Any family with fewer than 12 seedlings was removed from the data analysis. A family was classified as homozygous resistant (R) if more than 80% of the progenies were survived, homozygous susceptible (S) if less than 20% of the seedlings were alive, or segregating (Rs) if 21-79% were not dead (Gordon et al. 2006; Zhang et al. 2013).

The individual F2 progenies developed from the cross of PI 594527 and the susceptible cultivar 'Williams' were tested using isolate race 1, which was avirulent to most of the Rps genes. Among the 58 F2 progenies, 45 were resistant and 13 were susceptible. A segregation ratio of 45:13 fitted well with the Mendelian ratio of 3:1 ($\chi^2$=0.21, p=0.65) (Table 2). In order to get more accurate phenotypic results and heterozygous resistance information of F2 progenies, we thus advanced the rest of F2 population to the F2:3 generation, and subsequently ~12-36 F3 seedlings from each F2 plant were scored. The segregating ratio was further investigated in the F2:3 mapping population. The observed ratio of R (homozygous resistant):Rs (segragating):S (homozygous susceptible) was 59:102:48, which also fit well with the expected ratio of 1:2:1 ($\chi^2$=1.28, p=0.53). All these results suggested that the resistance to race 1 in PI 594527 was controlled by a single dominant novel resistance gene, which the inventors designated Rps11.

Example 3: Sample Collection and DNA Isolation

Young leaf tissues were collected in the greenhouse and maintained on ice until either kept in liquid nitrogen or

TABLE 1

Evaluation of soybean line PI 594527 for its interaction with different isolates of P. sojae.

| Isolate | Virulence Pathotype | No. of planted | No. of survived | No. of killed | Resistance to the isolate |
|---|---|---|---|---|---|
| Race 1 | 7 | 12 | 12 | 0 | Resistant |
| Race 10 | 1b, 3a, 3b, 3c, 5, 7 | 11 | 11 | 0 | Resistant |
| Race 13 | 4, 6, 7 | 11 | 11 | 0 | Resistant |
| Race 17 | 1b, 1d, 2, 3a, 3b, 3c, 4, 5, 6, 7, 8 | 12 | 12 | 0 | Resistant |
| Race 25 | 1a, 1b, 1c, 1k, 7 | 12 | 12 | 0 | Resistant |
| Race 28 | 1a, 1b, 1k, 2, 3c, 5, 7 | 10 | 9 | 1 | Resistant |
| ISA 19A-1 | 1a, 1b, 1k, 4, 6, 7 | 12 | 11 | 1 | Resistant |
| ISA 71D-1 | 1a, 1c, 1d, 7 | 11 | 10 | 1 | Resistant |
| ISA 33O-8 | 1a, 1b, 1c 1d, 1k, 3a, 3c, 4, 5, 7 | 11 | 11 | 0 | Resistant |
| Race 3* | 1a, 7 | — | — | — | Resistant |
| Race 7* | 1a, 2, 3a, 3c, 4, 5, 6, 7 | — | — | — | Resistant |

*Information obtained from the USDA-ARS Soybean Collection database

Example 2: Disease Inoculation and Evaluation

A modified hypocotyl inoculation technique was deployed for disease inoculation in all experiments (Dorrance et al. 2008). In short, seeds were planted and grown in stored in a −80° C. freezer before use. For F2:3 families, a mixture of equivalent amounts of leaf tissues were collected from the approximately 12-20 F3 seedlings. Those mixtures, to some degree, represented each F2 progenitor plant. Genomic DNA was extracted using the Cetyl Trimethyl Ammonium Bromide (CTAB) method with minor modifications (Allen et al. 2006). DNA concentration was determined using a Nanodrop ND-1000 Spectrophotometer (Thermo Fisher Scientific Inc., Wilmington, Del.). The final DNA concentration was adjusted to 50 ng/ul.

Example 4: Bulk Segregation Analysis Coupled with SNP Genotyping

To quickly identify the location of the loci associated with the Rps phenotype, the bulk segregant analysis (BSA) method was applied to the F2 segregation population (Michelmore et al. 1991). Resistant and susceptible bulks were formed by pooling equal amounts of DNA samples of either 10 resistant or 10 susceptible F2 individuals based on the inoculation results. Resistant and susceptible parental lines were also included for SNP genotyping. SNP genotyping was performed using the SoySNP8K BeadChip through the Illumina iScan platform (Illumina, Inc. San Diego, Calif.) at Michigan State University. The detailed Infinium II assay protocol was described by Song (Song et al. 2013). The SNP alleles were called using the GenomeStudio Genotyping Module v1.8.4 (Illumina, Inc. San Diego, Calif.).

Example 5: SSR Marker and PCR Analysis

SSR primers were obtained from Song (Song et al. 2010) and then synthesized by Integrated DNA Technologies, Inc (Coralville, Iowa). Polymorphic SSR markers between two parent lines were used in the experiments. PCR amplification was conducted according to Ping et al. 2014, with minor modifications. In brief, each PCR reaction contained 100 ng of template DNA, 10×PCR buffer (2.5 mM Mg2+), 0.2 mM dNTP, 0.2 µM forward and reverse primers, and 1.0 U of Taq DNA polymerase in a total volume of 20 µl. Reactions were performed on MyCycler thermo cycler (Bio-Rad Lab, Hercules, Calif.) consisting of an initial denaturation at 95° C. for 3 min, followed by 35 cycles of 95° C. for 30 s, 55-60° C. for 30 s and 72° C. for 30 s, with a final extension for 10 min at 72° C. The PCR products were mixed with 6× loading buffer and separated by 4% agarose gel (DOT Scientific Inc., Burton, Mich.) stained with ethidium bromide and then visualized on Molecular Imager Gel Doc XR system (Bio-Rad Lab, Hercules, Calif.). The SSR bands were then scored manually from the gel images.

Example 6: Data Analysis and Linkage Map Construction

The chi-square ($\chi^2$) analysis was performed to test the phenotypic data and genotypic data for a goodness-of-fit to the expected Mendelian ratio using the SPSS 22.0 software (SPSS, Chicago, USA) with a significance threshold of P=0.05. Markers that showed significant segregation distortion from the expected Mendelian ratios were excluded from map construction. A genetic linkage map was constructed using the Joinmap 4.1 software (Van Ooijen 2011). Linkage groups were determined using a logarithm of the odds (LOD) threshold of 3.0.

A total of 2588 SNPs, randomly distributed among the 20 chromosomes, were identified between the two parental lines. Based on the monogenic inheritance hypothesis, SNPs of the gene and its flanking regions detected in the susceptible F2 bulks were expected to be homozygous for a susceptibility allele inherited from the susceptible 'Williams' while other regions should be heterozygous since both alleles could received from the parents. However, SNPs of the resistant F2 bulks should always be heterozygous due to both homozygous resistant and heterozygous resistant F2 progenies were existed in the DNA pool. Therefore, the two bulks were genetically dissimilar in the target region while heterozygous at all other regions. Using this approach, a total genomic region ~5 Mb starting from 3 Mb to 8 Mb on chromosome 7 (MLG M) was identified as the potential location of the causative locus (FIG. 1). SNPs identified in this region are shown in Table 2.

To better map the novel Rps11 locus, the linkage analysis and genetic mapping were carried out with 209 F2:3 families derived from the cross. Based on the BSA results, 14 randomly distributed SSR primers were chosen from the tentative mapping region (Song et al. 2010). Four polymorphic SSR markers BARCSOYSSR_07_0223, BARCSOYSSR_07_0266, BARCSOYSSR_07_0278 and BARCSOYSSR_07_0459 were identified between the two parents of the mapping population. Then these four markers were used to genotype 50 of the F2:3 families. 9, 2, 0 and 14 recombinants were identified, respectively, indicating the Rps11 locus was between BARCSOYSSR_07_0223 and BARCSOYSSR_07_0459 and more linked to BARCSOYSSR_07_0266 and BARCSOYSSR_07_0278. The preliminary analysis also further confirmed the mapping results from the SNP-Chip analysis.

Subsequently, 9 polymorphic SSR markers located between SSR_07_0223 and SSR_07_0459 were selected to genotype the whole population. Chi-square analysis of the genotypic data from the 209 F2:3 families revealed that all nine polymorphic markers fit the expected 1:2:1 segregation ratio (Table 3). Therefore, a genetic map consisting of the 9 SSR markers and Rps11 was constructed using the Joinmap 4.1 software (Van Ooijen 2011). In this approach, the Rps locus was mapped to a 0.5 cM region, spanning 226 kb according to the Glyma1.1 reference genome, and flanked by SSR markers BARCSOYSSR_07_0286 and BARCSOYSSR_07_0300 (FIG. 2). SSR marker BARCSOYSSR_07_0295 was found to cosegregate with the locus.

TABLE 2

SNP markers identified in the PRSR resistance chromosome interval on chromosome 7. Genotypes of parents and susceptible and resistance bulks are listed. Physical positions of markers are based on Glyma1.1 soybean reference map.

| | | | Allele of samples | | | |
| --- | --- | --- | --- | --- | --- | --- |
| SNP ID | SEQ ID NO: | Chromosome Position (bp) | Williams | Susceptible Bulk | Resistant Bulk | PI 594527 |
| BARC_1.01_Gm07_5143130_A_G | 1 | 5143130 | AA | AA | AG | GG |
| BARC_1.01_Gm07_5330061_G_A | 2 | 5330061 | GG | GG | AG | AA |
| BARC_1.01_Gm07_5346264_G_A | 3 | 5346264 | GG | GG | AG | AA |
| BARC_1.01_Gm07_5352313_T_C | 4 | 5352313 | TT | TT | TC | CC |

TABLE 2-continued

SNP markers identified in the PRSR resistance chromosome interval on chromosome 7. Genotypes of parents and susceptible and resistance bulks are listed. Physical positions of markers are based on Glyma1.1 soybean reference map.

| | | | | Allele of samples | | |
|---|---|---|---|---|---|---|
| SNP ID | SEQ ID NO: | Chromosome Position (bp) | Williams | Susceptible Bulk | Resistant Bulk | PI 594527 |
| BARC_1.01_Gm07_5382683_C_T | 5 | 5382683 | CC | CC | TC | TT |
| BARC_1.01_Gm07_5383355_C_T | 6 | 5383355 | CC | CC | TC | TT |
| BARC_1.01_Gm07_5402911_T_C | 7 | 5402911 | TT | TT | TC | CC |
| BARC_1.01_Gm07_5442375_T_C | 8 | 5442375 | TT | TT | TC | CC |
| BARC_1.01_Gm07_5457696_C_T | 9 | 5457696 | CC | CC | TC | TT |
| BARC_1.01_Gm07_5481829_T_C | 10 | 5481829 | TT | TT | TC | CC |
| BARC_1.01_Gm07_5488504_A_G | 11 | 5488504 | AA | AA | AG | GG |
| BARC_1.01_Gm07_5490895_G_T | 12 | 5490895 | GG | GG | TT | TT |
| BARC_1.01_Gm07_5495895_G_A | 13 | 5495895 | GG | GG | AG | AA |
| BARC_1.01_Gm07_5500269_T_G | 14 | 5500269 | TT | TT | TG | TG |
| BARC_1.01_Gm07_5504994_G_T | 15 | 5504994 | GG | GG | TG | TT |
| BARC_1.01_Gm07_5519521_G_A | 16 | 5519521 | GG | GG | AG | AG |
| BARC_1.01_Gm07_5529382_A_G | 17 | 5529382 | AA | AA | AG | AG |
| BARC_1.01_Gm07_5555040_T_G | 18 | 5555040 | TT | TT | TG | TG |
| BARC_1.01_Gm07_5580414_T_C | 19 | 5580414 | TT | TT | CC | CC |
| BARC_1.01_Gm07_5599140_A_C | 20 | 5599140 | AA | AA | AC | AC |
| BARC_1.01_Gm07_5600654_A_G | 21 | 5600654 | AA | AA | AG | AG |
| BARC_1.01_Gm07_5601844_G_A | 22 | 5601844 | GG | GG | AG | AA |
| BARC_1.01_Gm07_5610838_T_C | 23 | 5610838 | TT | TT | TC | TC |
| BARC_1.01_Gm07_5629128_A_C | 24 | 5629128 | AA | AA | AC | AC |
| BARC_1.01_Gm07_5762798_C_T | 25 | 5762798 | CC | CC | TC | TT |
| BARC_1.01_Gm07_5835517_C_T | 26 | 5835517 | CC | CC | TC | TC |
| BARC_1.01_Gm07_5863012_C_A | 27 | 5863012 | CC | CC | AC | AA |
| BARC_1.01_Gm07_5900018_A_G | 28 | 5900018 | AA | AA | AG | GG |
| BARC_1.01_Gm07_5951000_G_A | 29 | 5951000 | GG | GG | AG | AA |
| BARC_1.01_Gm07_5963920_G_A | 30 | 5963920 | GG | GG | AG | AA |
| BARC_1.01_Gm07_5974721_A_G | 31 | 5974721 | AA | AA | AG | GG |
| BARC_1.01_Gm07_5989451_C_T | 32 | 5989451 | CC | CC | TC | TT |
| BARC_1.01_Gm07_6016358_A_G | 33 | 6016358 | AA | AA | AG | GG |

TABLE 3

Chi-square ($\chi^2$) goodness of fit test for the nine SSR markers in $F_{2:3}$ mapping population derived from PI 594527 × Williams.

| | Forward Primer | Reverse Primer | Observed | | | $\chi^2$ goodness of fit test | |
|---|---|---|---|---|---|---|---|
| | | | number$^a$ | | | 1:2:1 | |
| Marker | SEQ ID NO: | SEQ ID NO: | a | h | b | $\chi^2$ | p |
| BARCSOYSSR_07_0241 | 34 | 35 | 52 | 97 | 59 | 1.41 | 0.49 |
| BARCSOYSSR_07_0266 | 36 | 37 | 58 | 104 | 47 | 1.16 | 0.56 |
| BARCSOYSSR_07_0275 | 38 | 39 | 57 | 105 | 47 | 0.96 | 0.62 |
| BARCSOYSSR_07_0278 | 40 | 41 | 57 | 104 | 48 | 0.78 | 0.68 |
| BARCSOYSSR_07_0286 | 42 | 43 | 58 | 103 | 48 | 1 | 0.61 |
| BARCSOYSSR_07_0295 | 44 | 45 | 59 | 102 | 48 | 1.28 | 0.53 |
| BARCSOYSSR_07_0300 | 46 | 47 | 59 | 103 | 47 | 1.42 | 0.49 |
| BARCSOYSSR_07_0320 | 48 | 49 | 64 | 97 | 48 | 3.53 | 0.17 |
| BARCSOYSSR_07_0339 | 50 | 51 | 62 | 101 | 45 | 2.95 | 0.23 |

$^a$"a" is homozygous for the marker allele from the resistant PI 594527; "b" is homozygous for the marker allele from the susceptible Williams; "h" is heterozygous for the marker alleles from both parents.

Example 7: Fine Mapping the Rps11 QTL Region and Candidate Gene Prediction

The fine mapping population consists of 2640 F3 individuals derived from an initial cross between Williams and PI594527. Leaf samples were collected from each individual in the field for DNA isolation using a standard Cetyl Trimethyl Ammonium Bromide (CTAB) method. *P. sojae* race 1 was used for the resistance evaluation of the recombinants. All the inoculation work was performed using standard hypocotyl inoculation method as described by Lin et al. (2013). An F3:4 family was considered homozygous resistant if more than 80% of the progenies survived, heterozygous resistant if 21%-79% survived and susceptible if less than 20% survived.

SSR markers BARCSOYSSR_07_0286 and BARCSOYSSR_07_0300, which flank the Rps11 QTL on chromosome 7 and are separated by a physical distance of 225 kb based on the Glyma1.1 reference genome (Ping et al., 2015). These flanking markers were used to scan the whole F3 population to identify recombinants, resulting in the identification of 10 new recombinants. In addition to SSR markers, KASP™ markers and Insertion/Deletion (InDel) markers were also developed to genotype the recombinants. Rps11 was mapped into a 61 kb region defined by SSR marker BARCSOYSSR_07_0295 and an InDel marker InDel_1 (FIG. 3; Table 4). Within the 61 kb region, five gene models were predicted according to the new Glyma2.0 reference genome (Table 5). Based on the gene annotation, Glyma.07G062900 was the only gene that can encode a NB-ARC domain-containing disease resistance protein.

TABLE 4

Markers mapped to the 348 kb interval for PRSR resistance on chromosome 7. Genotypes of parents are listed. Markers fine mapped to the 61 kb interval are bolded. Physical positions of markers are based on Glyma2.0 reference genome.

| Marker Name | Marker Type | Chromosome Position (bp) | PI-594527 (Donor) Allele | Williams Allele | SNP Source Sequence SEQ ID NO: | SSR/InDel F Primer SEQ ID NO: | SSR/InDel R Primer SEQ ID NO: |
|---|---|---|---|---|---|---|---|
| BARC_1_01_Gm07_5383355_C_T | SNP | 5422037 | TT | CC | 6 | — | — |
| BARCSOYSSR_07_0286 | SSR | 5424576 | smaller band | | — | 42 | 43 |
| BARCSOYSSR_07_0289 | SSR | 5443168 | smaller band | | — | 52 | 53 |
| BARC_1_01_Gm07_5442375_T_C | SNP | 5481057 | CC | TT | 8 | — | — |
| BARC_1_01_Gm07_5457696_C_T | SNP | 5496333 | TT | CC | 9 | — | — |
| Gm0_5480878_G_A | SNP | 5519515 | AA | GG | 54 | — | — |
| BARC_1_01_Gm07_5481829_T_C | SNP | 5520466 | CC | TT | 10 | — | — |
| BARCSOYSSR_07_0295 | SSR | 5523049 | smaller band | | — | 44 | 45 |
| BARC_1_01_Gm07_5488504_A_G | SNP | 5527141 | GG | AA | 11 | — | — |
| BARC_1_01_Gm07_5490895_G_T | SNP | 5529532 | TT | GG | 12 | — | — |
| BARC_1_01_Gm07_5495895_G_A | SNP | 5534532 | AA | GG | 13 | — | — |
| BARC_1_01_Gm07_5500269_T_G | SNP | 5538906 | GG | TT | 14 | — | — |
| BARC_1_01_Gm07_5504994_G_T | SNP | 5543631 | TT | GG | 15 | — | — |
| BARC_1_01_Gm07_5519521_G_A | SNP | 5558158 | AA | GG | 16 | — | — |
| InDel_2 | InDel | 5570449 | larger band | | — | 55 | 56 |
| InDel_1 | InDel | 5584923 | larger band | | — | 57 | 58 |
| BARCSOYSSR_07_0297 | SSR | 5593457 | smaller band | | — | 59 | 60 |
| BARC_1_01_Gm07_5555040_T_G | SNP | 5595105 | GG | TT | 18 | — | — |
| BARC_1_01_Gm07_5580414_T_C | SNP | 5618417 | CC | TT | 19 | — | — |
| BARC_1_01_Gm07_5762798_C_T | SNP | 5731433 | TT | CC | 25 | — | — |
| BARC_1_01_Gm07_5599140_A_C | SNP | 5760845 | CC | AA | 20 | — | — |
| BARC_1_01_Gm07_5601844_G_A | SNP | 5763549 | AA | GG | 22 | — | — |
| BARC_1_01_Gm07_5610838_T_C | SNP | 5772544 | CC | TT | 23 | — | — |
| BARCSOYSSR_07_0300 | SSR | 5773063 | smaller band | | — | 46 | 47 |
| BARC_1_01_Gm07_5629128_A_C | SNP | 5790834 | CC | AA | 24 | — | — |

TABLE 5

Gene annotation in the 61 kb mapped region according to the soybean reference genome (Glyma2.0).

| Gene ID | Functional Annotation |
|---|---|
| Glyma.07G62500 | GRIP-related ARF-binding domain-containing protein |
| Glyma.07G62600 | Reticulon family protein |
| Glyma.07G62700 | S-adenosyl-L-methionine-dependent methyltransferases superfamily protein |
| Glyma.07G62800 | RING/U-box superfamily protein |
| Glyma.07G62900 | NB-ARC domain-containing disease resistance protein |

Marker Framework and Use for Marker Assisted Selection

A set of common markers can be used to establish a framework for identifying markers in the chromosome interval. Table 4 shows markers that are in consistent position relative to one another on the derived genetic linkage map of chromosome 7. Physical positions of SSR markers are determined by BLAST searching their primer sequences against soybean reference genomes, Glyma 1.1 or Glyma2.0, which are publicly available on the SoyBase website.

Closely linked markers flanking the locus of interest that have alleles in linkage disequilibrium with a favorable allele at that locus may be effectively used to select for progeny plants with increased PRSR resistance. Thus, the markers described herein, such as those listed in Table 6, as well as other markers genetically or physically mapped to the same chromosomal segment, may be used to select for soybean plants with increased PRSR resistance. Typically, a set of these markers will be used (e.g. 2 or more, 3 or more, 4 or more, 5 or more) in the regions flanking the locus of interest. Optionally, a marker within the actual gene and/or locus may be used.

TABLE 6

Molecular markers in the PRSR resistance interval on chromosome 7 and their donor allele. Markers within the chromosome interval are desirable for marker assisted selection.

| Marker Name | Marker Type | PI-594527 (Donor) Allele | SNP Source Sequence SEQ ID NO: | SSR/InDel F Primer SEQ ID NO: | SSR/InDel R Primer SEQ ID NO: |
|---|---|---|---|---|---|
| BARC_1_01_Gm07_5383355_C_T | SNP | TT | 6 | — | — |
| BARCSOYSSR_07_0286 | SSR | smaller band | — | 42 | 43 |
| BARCSOYSSR_07_0289 | SSR | smaller band | — | 52 | 53 |
| BARC_1_01_Gm07_5442375_T_C | SNP | CC | 8 | — | — |
| BARC_1_01_Gm07_5457696_C_T | SNP | TT | 9 | — | — |
| Gm07_5480878_G_A | SNP | AA | 54 | — | — |
| BARC_1_01_Gm07_5481829_T_C | SNP | CC | 10 | — | — |
| BARCSOYSSR_07_0295 | SSR | smaller band | — | 44 | 45 |
| BARC_1_01_Gm07_5488504_A_G | SNP | GG | 11 | — | — |
| BARC_1_01_Gm07_5490895_G_T | SNP | TT | 12 | — | — |
| BARC_1_01_Gm07_5495895_G_A | SNP | AA | 13 | — | — |
| BARC_1_01_Gm07_5500269_T_G | SNP | GG | 14 | — | — |
| BARC_1_01_Gm07_5504994_G_T | SNP | TT | 15 | — | — |

TABLE 6-continued

Molecular markers in the PRSR resistance interval on chromosome 7 and their donor allele.
Markers within the chromosome interval are desirable for marker assisted selection.

| Marker Name | Marker Type | PI-594527 (Donor) Allele | SNP Source Sequence SEQ ID NO: | SSR/InDel F Primer SEQ ID NO: | SSR/InDel R Primer SEQ ID NO: |
|---|---|---|---|---|---|
| BARC_1_01_Gm07_5519521_G_A | SNP | AA | 16 | — | — |
| InDel_2 | InDel | larger band | — | 55 | 56 |
| InDel_1 | InDel | larger band | — | 57 | 58 |
| BARCSOYSSR_07_0297 | SSR | smaller band | — | 59 | 60 |
| BARC_1_01_Gm07_5555040_T_G | SNP | GG | 18 | — | — |
| BARC_1_01_Gm07_5580414_T_C | SNP | CC | 19 | — | — |
| BARC_1_01_Gm07_5762798_C_T | SNP | TT | 25 | — | — |
| BARC_1_01_Gm07_5599140_A_C | SNP | CC | 20 | — | — |
| BARC_1_01_Gm07_5601844_G_A | SNP | AA | 22 | — | — |
| BARC_1_01_Gm07_5610838_T_C | SNP | CC | 23 | — | — |
| BARCSOYSSR_07_0300 | SSR | smaller band | — | 46 | 47 |
| BARC_1_01_Gm07_5629128_A_C | SNP | CC | 24 | — | — |

REFERENCES

Allen G, Flores-Vergara M, Krasynanski S, Kumar S, Thompson W (2006) A modified protocol for rapid DNA isolation from plant tissues using cetyltrimethylammonium bromide Nature protocols 1:2320-2325

Demirbas A et al. (2001) Simple sequence repeat markers linked to the soybean genes for *Phytophthora* resistance Crop Sci 41:1220-1227

Dorrance A, Mills D, Robertson A, Draper M, Giesler L, Tenuta A (2007) *Phytophthora* root and stem rot of soybean The Plant Health Instructor 10

Dorrance A, Schmitthenner A (2000) New sources of resistance to *Phytophthora sojae* in the soybean plant introductions Plant Dis 84:1303-1308

Dorrance A E, Berry S A, Anderson T R, Meharg C (2008) Isolation, storage, pathotype characterization, and evaluation of resistance for *Phytophthora sojae* in soybean Plant Health Progress 10:1094

Ellis J, Dodds P, Pryor T (2000) Structure, function and evolution of plant disease resistance genes Curr Opin Plant Biol 3:278-284

Erwin D C, Ribeiro O K (1996) *Phytophthora* diseases worldwide. American Phytopathological Society (APS Press), Fan A, Wang X, Fang X, Wu X, Zhu Z (2009) Molecular identification of *Phytophthora* resistance gene in soybean cultivar Yudou 25 Acta Agronomica Sinica 35:1844-1850

Ganal M W et al. (2011) A large maize (*Zea mays* L.) SNP genotyping array: development and germplasm genotyping, and genetic mapping to compare with the B73 reference genome PloS one 6:e28334

Gao H, Narayanan N N, Ellison L, Bhattacharyya M K (2005) Two classes of highly similar coiled coil-nucleotide binding-leucine rich repeat genes isolated from the Rps1-k locus encode *Phytophthora* resistance in soybean Mol Plant-Microbe Interact 18:1035-1045

Gordon S G, Martin S K S, Dorrance A E (2006) Rps8 maps to a resistance gene rich region on soybean molecular linkage group F Crop Sci 46:168-173 doi:DOI 10.2135/cropsci2004.04-0024

Kanazin V, Marek L F, Shoemaker R C (1996) Resistance gene analogs are conserved and clustered in soybean Proceedings of the National Academy of Sciences 93:11746-11750

Kaufmann M J, Gerdemann J (1958) Root and stem rot of soybean caused by *Phytophthora sojae* n. sp Phytopathology 48:201-208.

Kim K-S et al. (2010) Fine mapping the soybean aphid resistance gene Rag1 in soybean Theor Appl Genet 120:1063-1071

Koenning S R, Wrather J A (2010) Suppression of soybean yield potential in the continental United States by plant diseases from 2006 to 2009 Plant Health Prog http://dx doi org/101094/PHP-2010-1122-01-RS Li Y, Hill C B, Carlson S R, Diers B W, Hartman G L (2007) Soybean aphid resistance genes in the soybean cultivars Dowling and Jackson map to linkage group M Mol Breed 19:25-34

Lin F et al. (2013) Molecular mapping of two genes conferring resistance to *Phytophthora sojae* in a soybean landrace P I 567139B Theor Appl Genet 126:2177-2185

McDonald B A, Linde C (2002) Pathogen population genetics, evolutionary potential, and durable resistance Annu Rev Phytopathol 40:349-379

Michelmore R W, Meyers B C (1998) Clusters of resistance genes in plants evolve by divergent selection and a birth-and-death process Genome Res 8:1113-1130

Michelmore R W, Paran I, Kesseli R (1991) Identification of markers linked to disease-resistance genes by bulked segregant analysis: a rapid method to detect markers in specific genomic regions by using segregating populations Proceedings of the National Academy of Sciences 88:9828-9832

Ping J et al. (2014) Dt2 is a gain-of-function MADS-domain factor gene that specifies semideterminacy in soybean The Plant Cell Online 26:2831-2842

Polzin K, Lohnes D, Nickell C, Shoemaker R (1994) Integration of Rps2, Rmd, and Rj2 into linkage group J of the soybean molecular map J Hered 85:300-303

Sandhu D, Gao H, Cianzio S, Bhattacharyya M K (2004) Deletion of a disease resistance nucleotide-binding-site leucine-rich-repeat-like sequence is associated with the loss of the *Phytophthora* resistance gene Rps4 in soybean Genetics 168:2157-2167

Saruta M et al. (2012) Screening and genetic analysis of resistance to peanut stunt virus in soybean: identification of the putative Rpsv1 resistance gene Breeding science 61:625

Schmitthenner A (1999) *Phytophthora* rot of soybean Compendium of soybean diseases, 4th edn The American Phytopathological Society Press, St Paul:39-42

Schmitthenner A F (1985) Problems and Progress in Control of *Phytophthora* Root-Rot of Soybean Plant Dis 69:362-368 doi:Doi 10.1094/Pd-69-362

Song Q, Hyten D L, Jia G, Quigley C V, Fickus E W, Nelson R L, Cregan P B (2013) Development and evaluation of SoySNP50K, a high-density genotyping array for soybean PloS one 8:e54985

Song Q J et al. (2010) Abundance of SSR Motifs and Development of Candidate Polymorphic SSR Markers (BARCSOYSSR_1.0) in Soybean Crop Sci 50:1950-1960 doi:DOI 10.2135/cropsci2009.10.0607

Sugimoto T et al. (2011) Genetic analysis and identification of DNA markers linked to a novel *Phytophthora sojae* resistance gene in the Japanese soybean cultivar Waseshiroge Euphytica 182:133-145

Sun J, Li L, Zhao J, Huang J, Yan Q, Xing H, Guo N (2014) Genetic analysis and fine mapping of RpsJS, a novel resistance gene to *Phytophthora sojae* in soybean [*Glycine max* (L.) Merr.] Theor Appl Genet 127:913-919

Sun S et al. (2011) Characterization and mapping of RpsYu25, a novel resistance gene to *Phytophthora sojae* Plant breeding 130:139-143

Tian Z et al. (2010) Artificial selection for determinate growth habit in soybean P Natl Acad Sci USA 107:8563-8568 doi: 10.1073/pnas.1000088107

Van Ooijen J (2011) Multipoint maximum likelihood mapping in a full-sib family of an outbreeding species Genetics research 93:343-349

Wang S et al. (2014) Characterization of polyploid wheat genomic diversity using a high-density 90 000 single nucleotide polymorphism array Plant Biotechnol J Weng C, Yu K, Anderson T, Poysa V (2001) Mapping genes conferring resistance to *Phytophthora* root rot of soybean, Rps1a and Rps7 J Hered 92:442-446

Wrather J, Koenning S (2009) Effects of diseases on soybean yields in the United States 1996 to 2007 Plant Health Progress Wu X et al. (2011a) Identification, Genetic Analysis and Mapping of Resistance to *Phytophthora sojae* of Pm28 in Soybean Agricultural Sciences in China 10:1506-1511

Wu X, Zhou B, Sun S, Zhao J, Chen S, Gai J, Xing H (2011b) Genetic analysis and mapping of resistance to *Phytophthora sojae* of Pm14 in soybean Scientia Agricultura Sinica 44:456-460

Yao H, Wang X, Wu X, Xiao Y, Zhu Z (2010) Molecular mapping of *Phytophthora* resistance gene in soybean cultivar zaoshu18 Journal of Plant Genetic Resources 11:213-217

Zhang J, Xia C, Wang X, Duan C, Sun S, Wu X, Zhu Z (2013) Genetic characterization and fine mapping of the novel *Phytophthora* resistance gene in a Chinese soybean cultivar Theor Appl Genet 126:1555-1561

Zhang X, Feng Y, Cheng H, Tian D, Yang S, Chen J-Q (2011) Relative evolutionary rates of NBS-encoding genes revealed by soybean segmental duplication Mol Genet Genomics 285:79-90

Zhao K et al. (2011) Genome-wide association mapping reveals a rich genetic architecture of complex traits in *Oryza sativa* Nature communications 2:467

Zhu Z, Huo Y, Wang X, Huang J, Wu X (2007) Molecular identification of a novel *Phytophthora* resistance gene in soybean

---

We claim:

1. A method of identifying and harvesting seed of a soybean plant that displays increased *Phytophthora* root and stem rot (PRSR) resistance, the method comprising:
   isolating nucleic acid from a soybean plant;
   genotyping the nucleic acid;
   detecting at least one allele of at least one marker locus in the genotyped nucleic acid and thereby identifying a soybean plant that displays increased PRSR resistance; and
   harvesting seed from the soybean plant that displays increased PRSR resistance, wherein:
   a. the marker locus is BARCSOYSSR_07_0241, BARCSOYSSR_07_0266, BARCSOYSSR_07_0275, BARCSOYSSR_07_0278, BARCSOYSSR_07_0286, BARCSOYSSR_07_0295, BARCSOYSSR_07_0300, BARCSOYSSR_07_0320, or BARCSOYSSR_07_0339; and
   b. the at least one allele is associated with increased PRSR resistance.

2. The method of claim 1, wherein the marker locus is BARCSOYSSR_07_0295, BARCSOYSSR_07_0300, or BARCSOYSSR_07_0320.

3. The method of claim 1, wherein the at least one marker locus is BARCSOYSSR_07_0286, BARCSOYSSR_07_0300 or BARCSOYSSR_07_0320.

4. The method of claim 3, wherein the at least one marker locus is BARCSOYSSR_07_0300.

5. A method of identifying and harvesting seed of a soybean plant that displays increased *Phytophthora* root and stem rot (PRSR) resistance, the method comprising:
   isolating nucleic acid from a soybean plant;
   genotyping the nucleic acid;
   detecting a haplotype comprising alleles at one or more marker loci in the genotyped nucleic acid and thereby identifying a soybean plant that displays increased PRSR resistance; and
   harvesting seed from the soybean plant that displays increased PRSR resistance, wherein
   a. the haplotype comprises alleles at one or more marker loci selected from the group consisting of BARCSOYSSR_07_0241, BARCSOYSSR_07_0266, BARCSOYSSR_07_0275, BARCSOYSSR_07_0278, BARCSOYSSR_07_0286, BARCSOYSSR_07_0295, BARCSOYSSR_07_0300, BARCSOYSSR_07_0320, and BARCSOYSSR_07_0339; and,
   b. the haplotype comprises alleles which are associated with increased PRSR resistance.

6. The method of claim 5, wherein the haplotype comprises alleles at one or more marker loci selected from the group consisting of BARCSOYSSR_07_0289, BARCSOYSSR_07_0295, BARCSOYSSR_07_0297, BARCSOYSSR_07_0300, and BARCSOYSSR_07_0320.

7. The method of claim 5, wherein the at least one marker locus is BARCSOYSSR_07_0300.

8. The method of claim 5, wherein the at least one marker locus is BARCSOYSSR_07_0286, BARCSOYSSR_07_0300, or BARCSOYSSR_07_0320.

9. A method of marker assisted selection comprising:
   a. obtaining a first soybean plant having at least one allele of a marker locus, wherein the marker locus is BARCSOYSSR_07_0241, BARCSOYSSR_07_0266, BARCSOYSSR_07_0275, BARCSOYSSR_07_0278, BARCSOYSSR_07_0286, BARCSOYSSR_07_0295, BARCSOYSSR_07_0300, BARCSOYSSR_07_0320, or BARCSOYSSR_07_0339 and the allele of the marker locus is associated with increased *Phytophthora* root and stem rot (PRSR) resistance;

b. crossing the first soybean plant to a second soybean plant to produce one or more progeny plants, wherein the second soybean plant does not comprise the at least one allele of a marker locus associated with increased PRSR resistance;

c. isolating nucleic acid from the one or more progeny plants and genotyping the isolated nucleic acid to detect the at least one allele; and d. selecting one or more of the progeny plants with having nucleic acid comprising the at least one allele and thereby selecting a soybean plant that displays increased PRSR resistance.

10. The method of claim 9, wherein the marker locus is BARCSOYSSR_07_0295, BARCSOYSSR_07_0300, or BARCSOYSSR_07_0320.

11. The method of claim 9, wherein the at least one marker locus is BARCSOYSSR_07_0300.

12. The method of claim 9, wherein the at least one marker locus is BARCSOYSSR_07_0286, BARCSOYSSR_07_0300, or BARCSOYSSR_07_0320.

13. The method of claim 1, wherein the at least one marker locus is BARCSOYSSR_07_0320.

* * * * *